(12) United States Patent
Wang et al.

(10) Patent No.: US 7,978,895 B2
(45) Date of Patent: Jul. 12, 2011

(54) X-RAY CT SYSTEM

(75) Inventors: Xueli Wang, Beijing (CN); Akihiko Nishide, Tokyo (JP); Akira Hagiwara, Tokyo (JP); Kotoko Morikawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 906 days.

(21) Appl. No.: 11/552,656

(22) Filed: Oct. 25, 2006

(65) Prior Publication Data

US 2007/0098241 A1 May 3, 2007

(30) Foreign Application Priority Data

Oct. 27, 2005 (CN) .......................... 2005 1 0118513

(51) Int. Cl.
  *G06K 9/00* (2006.01)
  *A61B 5/05* (2006.01)
  *A61B 8/00* (2006.01)
(52) U.S. Cl. ........ 382/131; 382/128; 382/129; 382/130; 382/132; 600/407; 600/443
(58) Field of Classification Search .......... 382/128–132; 378/4, 19; 600/407, 443
  See application file for complete search history.

(56) References Cited

U.S. PATENT DOCUMENTS

| | | | |
|---|---|---|---|
| 4,583,538 A * | 4/1986 | Onik et al. ..................... 606/130 |
| 5,170,346 A | 12/1992 | Crawford et al. | |
| 5,270,923 A | 12/1993 | King et al. | |
| 5,579,358 A | 11/1996 | Lin | |
| 5,835,559 A | 11/1998 | Hsieh | |
| 6,252,924 B1 | 6/2001 | Davantes et al. | |
| 2002/0131549 A1* | 9/2002 | Oikawa ........................... 378/19 |
| 2004/0002641 A1* | 1/2004 | Sjogren et al. ................ 600/407 |
| 2004/0156469 A1* | 8/2004 | Nishide et al. ................... 378/19 |
| 2005/0090743 A1* | 4/2005 | Kawashima et al. ......... 600/443 |
| 2007/0081704 A1* | 4/2007 | Pan et al. ....................... 382/128 |

FOREIGN PATENT DOCUMENTS

| | | |
|---|---|---|
| JP | 04-044743 | 2/1992 |
| JP | 06-260075 A1 | 9/1994 |
| JP | 08-117218 | 5/1996 |
| JP | 2001-104291 | 4/2001 |
| JP | 2003334188 | 11/2003 |

OTHER PUBLICATIONS

Japan Patent Office, Notice of Reasons for Rejection for Application No. 2006-137686, Oct. 19, 2010, 2 pages, JP.

* cited by examiner

*Primary Examiner* — Vu Le
*Assistant Examiner* — Amara Abdi
(74) *Attorney, Agent, or Firm* — Armstrong Teasdale LLP

(57) ABSTRACT

The present invention is intended to improve the quality of a three-dimensional display image, an MPR display image, or an MIP display image presented by an X-ray CT system that performs a conventional (axial) scan, a cine scan, or a helical scan. The X-ray CT system includes an image reconstruction unit or an image display unit. The image reconstruction unit or image display unit measures deviations of tomographic images in an x direction that is a horizontal direction and deviations thereof in a y direction that is a vertical direction according to the continuity in a z direction of an object that exhibits high CT numbers and that is visualized as a reference in the tomographic images; such as, a cradle, a head holder, the surface of a subject's body, or a bone. The image reconstruction unit or image display unit then compensates the deviations.

19 Claims, 24 Drawing Sheets

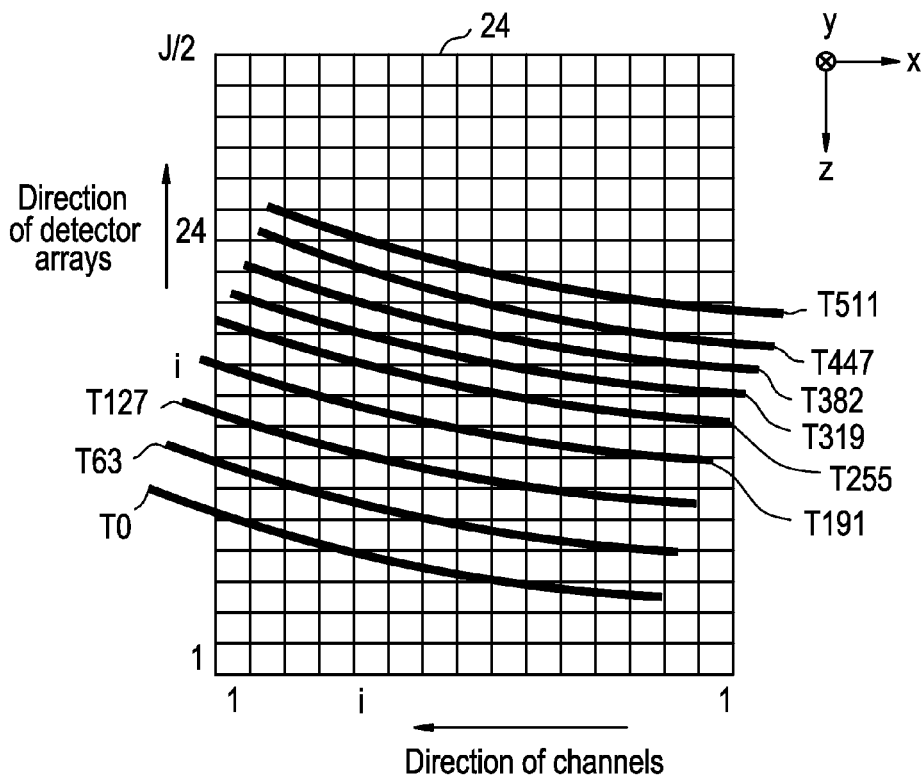
FIG. 7
FIG. 8
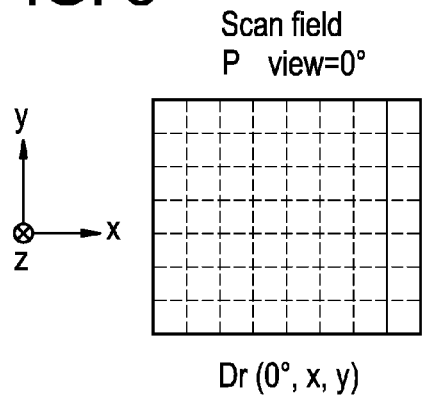
FIG. 9
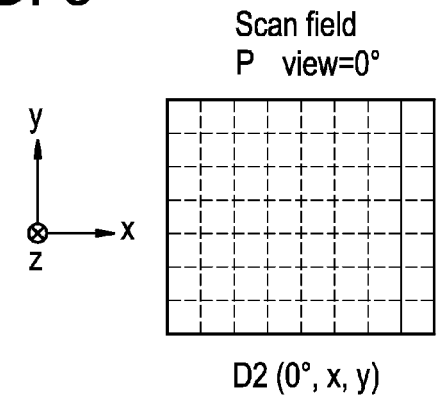
FIG. 10
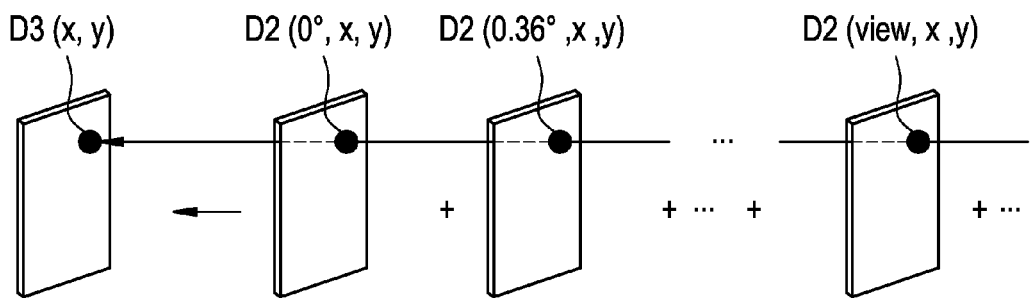

FIG. 13

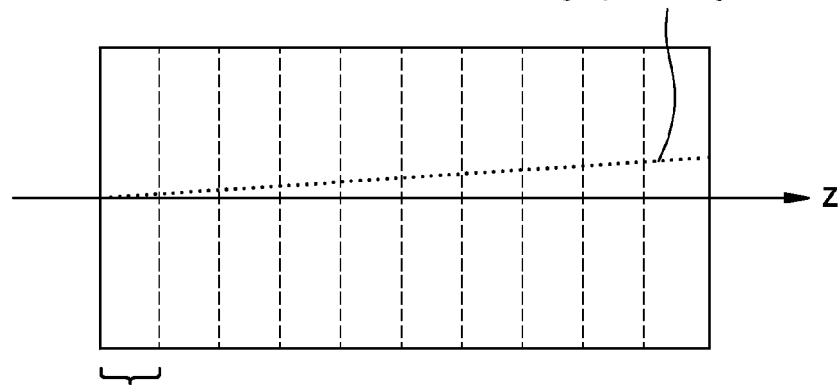

Deviation of locus of centers of tomographic images

For example conventional (axial) scanning or cine scanning that produces 64 tomographic images during one scan Deviations of centers of tomographic images produced by axial scan which are observed in conventional three-dimensional display image, MPR display image, or MIP display image.

FIG. 14

Equal to or smaller than D

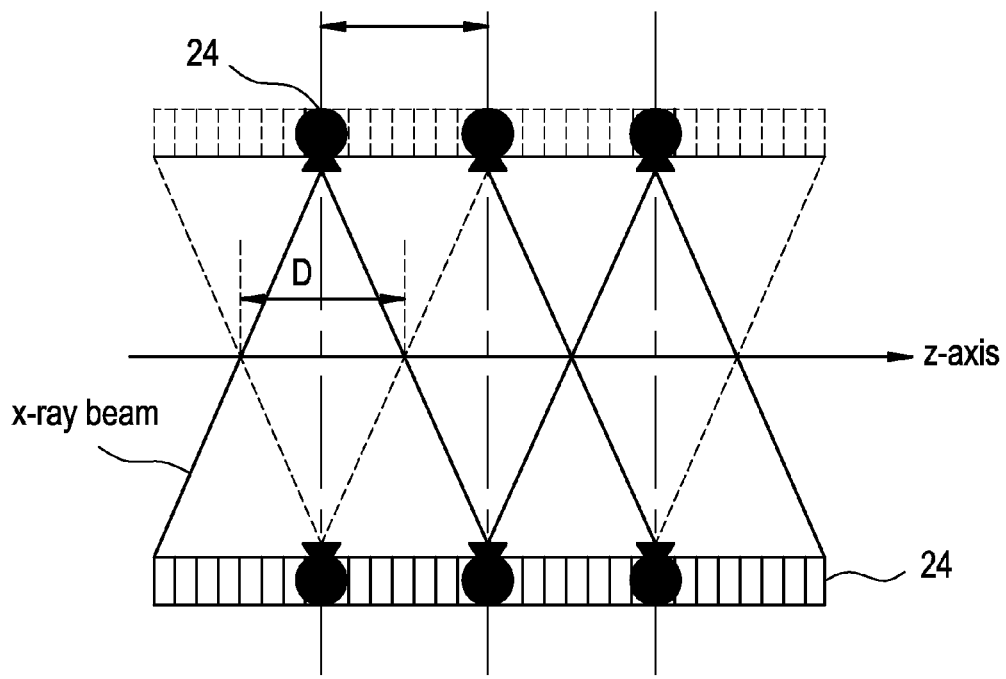

Conventional (Axial) scan or cine scan continuously performed in z direction

FIG. 15

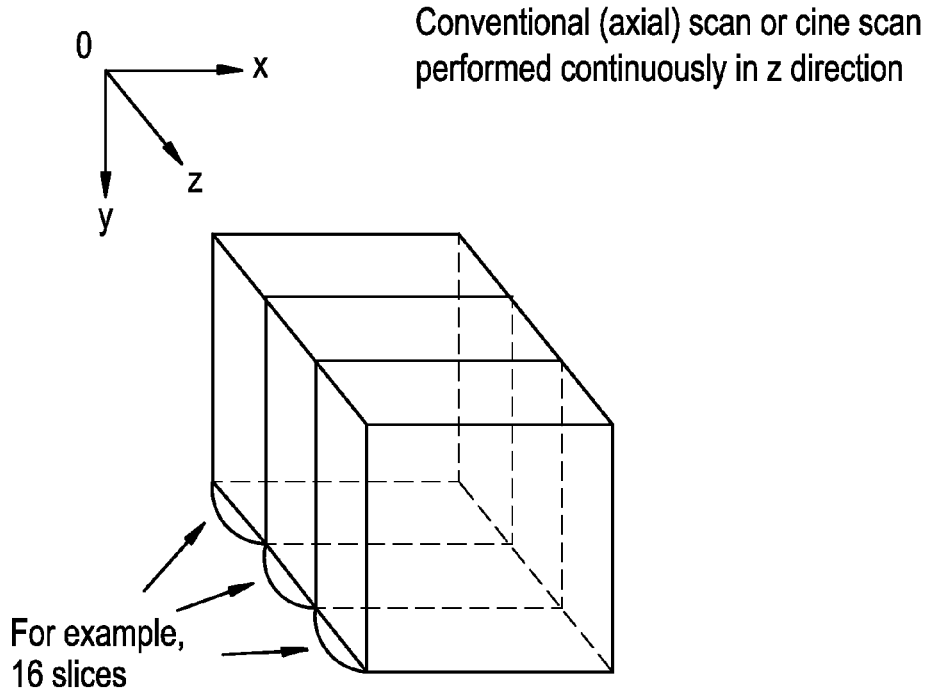

Conventional (axial) scan or cine scan performed continuously in z direction

For example, 16 slices

FIG. 16

Conventional (axial) scan or cine scan performed continuously in z direction so that successive scan will partly coincide with one another

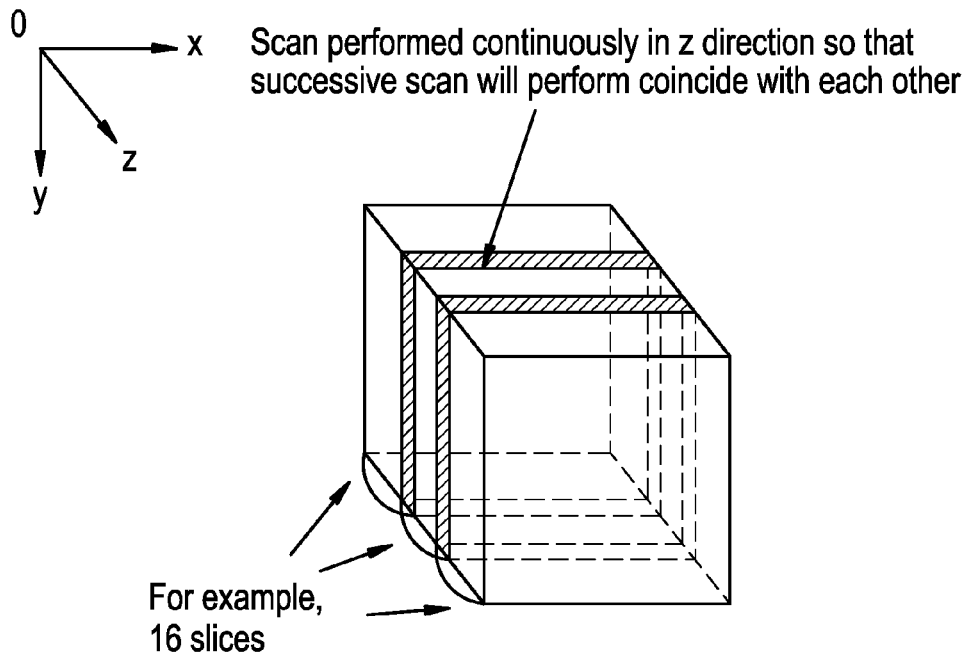

Scan performed continuously in z direction so that successive scan will perform coincide with each other For example, 16 slices

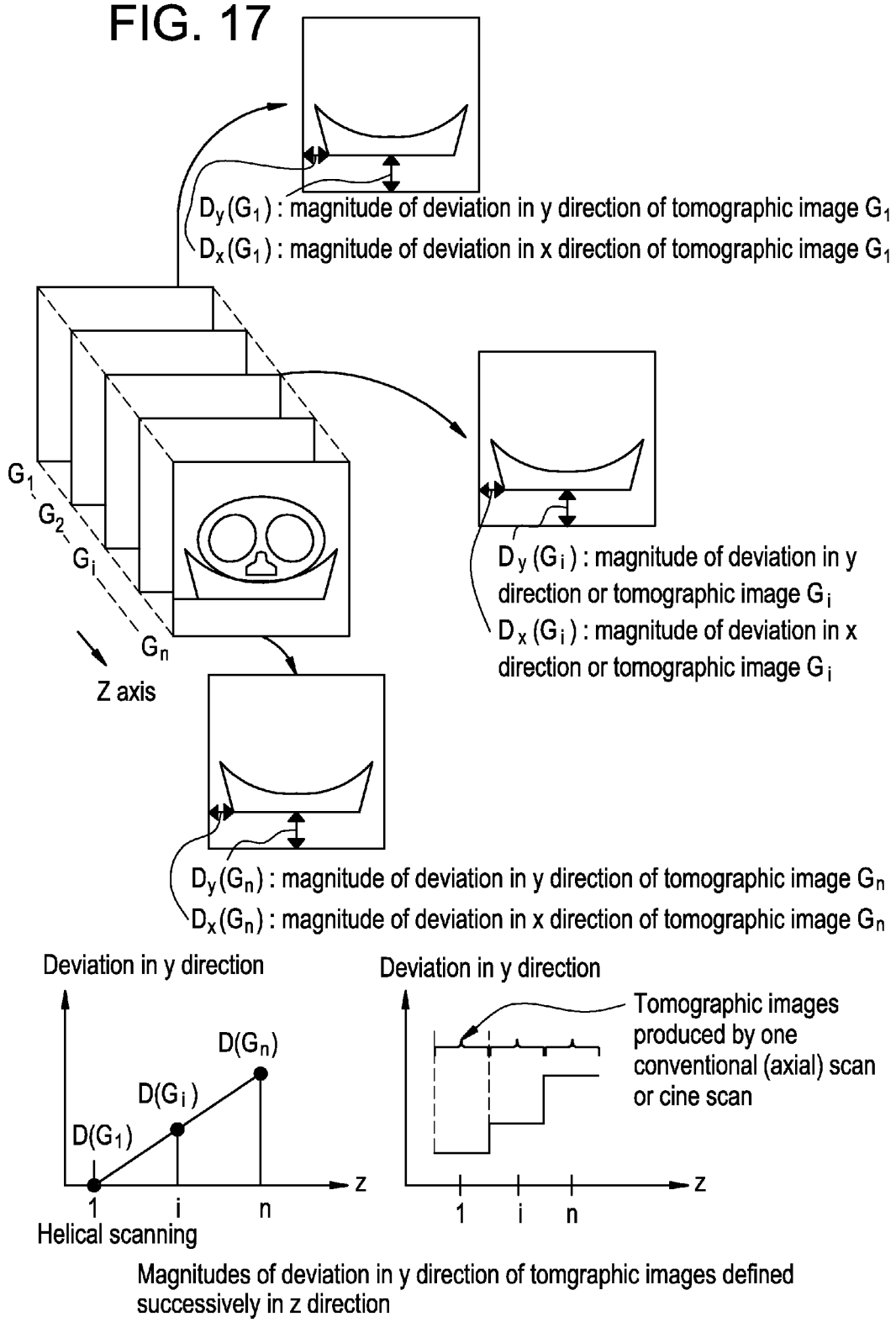

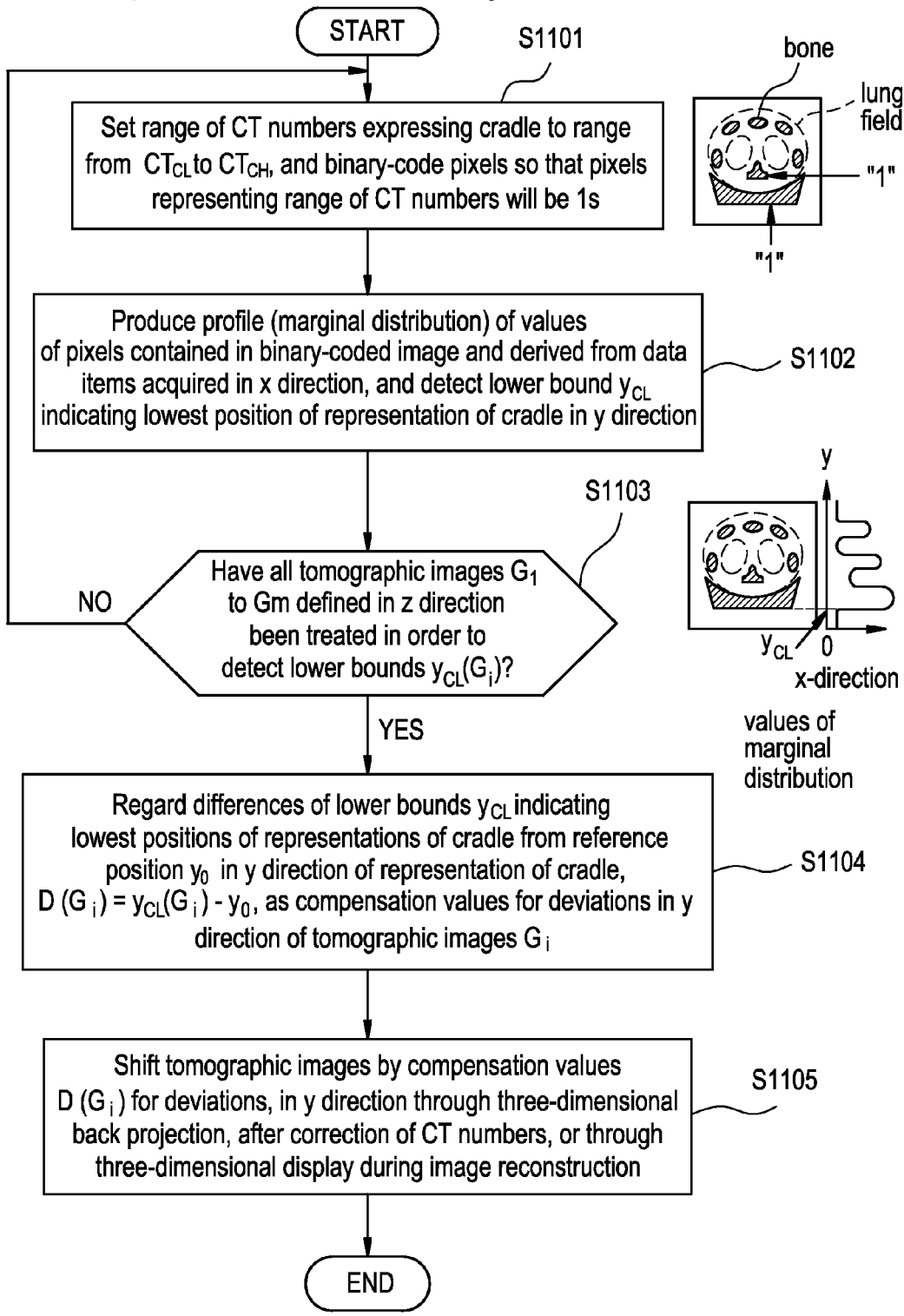

FIG. 19

Compensation of deviations in x and y directions through characteristic parameter extraction based on marginal distribution measurement (Part 1)

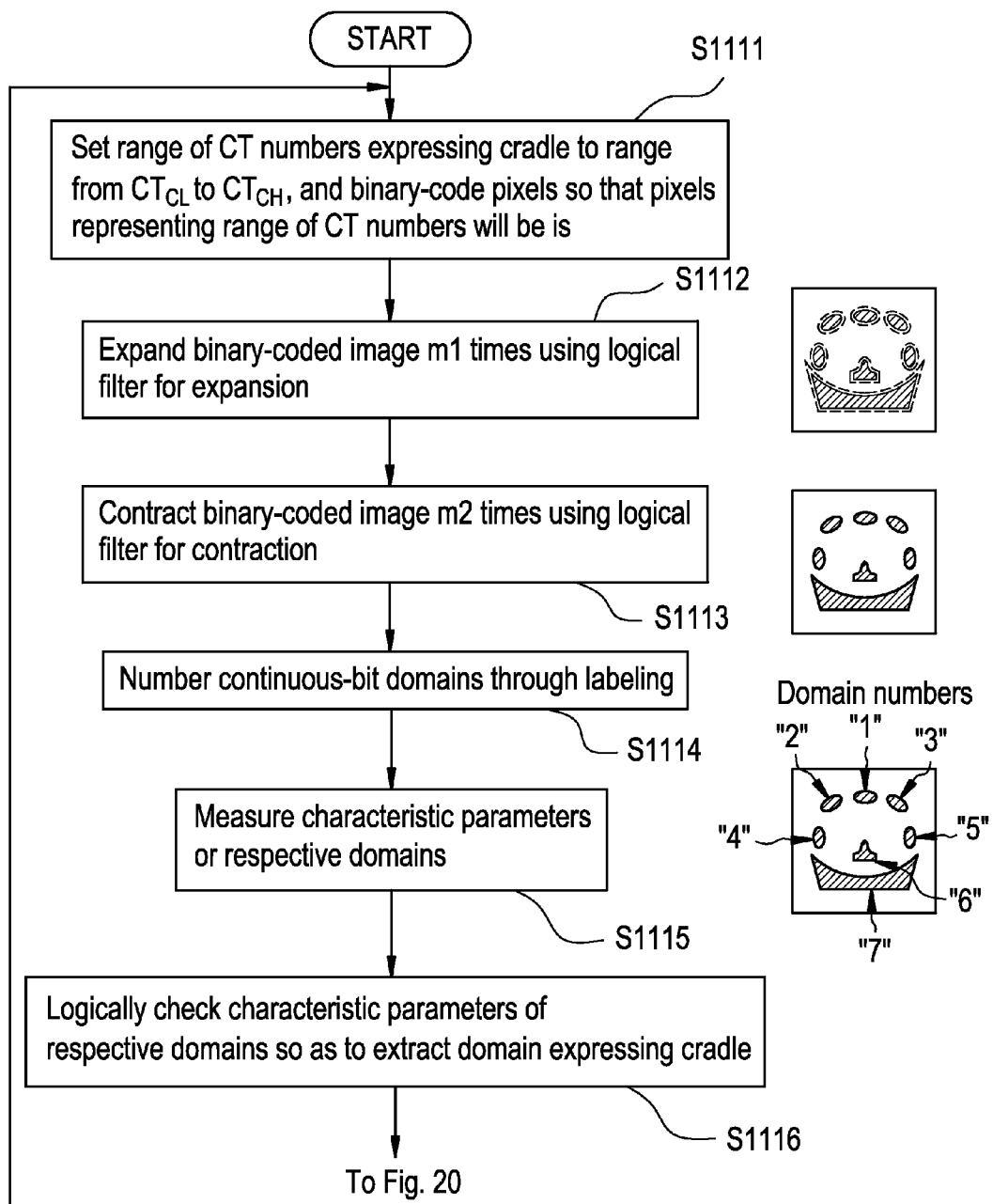

START

S1111: Set range of CT numbers expressing cradle to range from $CT_{CL}$ to $CT_{CH}$, and binary-code pixels so that pixels representing range of CT numbers will be is S1112: Expand binary-coded image m1 times using logical filter for expansion S1113: Contract binary-coded image m2 times using logical filter for contraction S1114: Number continuous-bit domains through labeling Domain numbers "2" "1" "3" "4" "5" "6" "7"

S1115: Measure characteristic parameters or respective domains

S1116: Logically check characteristic parameters of respective domains so as to extract domain expressing cradle To Fig. 20

From Fig. 20

Compensation of deviations in x and y directions through chracteristic parameter extraction based on marginal distribution measurement (Part 2)

FIG. 21

Logical filter for expansion

| x | 1 | x |
|---|---|---|
| x | x | x |
| x | x | x |

| x | x | x |
|---|---|---|
| x | x | 1 |
| x | x | x |

| x | x | x |
|---|---|---|
| x | x | x |
| x | 1 | x |

| x | x | x |
|---|---|---|
| 1 | x | x |
| x | x | x |

Logical filter for expansion treating four neighborhoods

Note: x may be a 1 or 0

| x | 1 | x | x | x | x | x | x | x | x | x | x | x | x | x | x | x | x | x | x | x | 1 | x | x |
|---|---|---|---|---|---|---|---|---|---|---|---|---|---|---|---|---|---|---|---|---|---|---|---|
| x | x | x | x | x | 1 | x | x | x | x | x | x | x | x | x | x | x | x | 1 | x | x | x | x | x |
| x | x | x | x | x | x | x | x | 1 | x | 1 | x | 1 | x | x | 1 | x | x | x | x | x | x | x | x |

Logical filter for expansion treating eight neighborhoods

FIG. 22

Logical filter for contraction

| x | 0 | x |
|---|---|---|
| x | x | x |
| x | x | x |

| x | x | x |
|---|---|---|
| x | x | 0 |
| x | x | x |

| x | x | x |
|---|---|---|
| x | x | x |
| x | 0 | x |

| x | x | x |
|---|---|---|
| 0 | x | x |
| x | x | x |

Logical filter for expansion treating four neighbourhoods

Note: x may be a 1 or 0

| x | 0 | x | x | x | 0 | x | x | x | x | x | x | x | x | x | x | x | x | x | x | x | 0 | x | x |
|---|---|---|---|---|---|---|---|---|---|---|---|---|---|---|---|---|---|---|---|---|---|---|---|
| x | x | x | x | x | x | x | x | 0 | x | x | x | x | x | x | x | x | x | 0 | x | x | x | x | x |
| x | x | x | x | x | x | x | x | x | x | 0 | x | 0 | x | 0 | x | x | x | x | x | x | x | x | x |

Logical filter for expansion treating eight neighborhoods

Compensation of deviation in x and y directions according to pattern matching method

FIG. 24

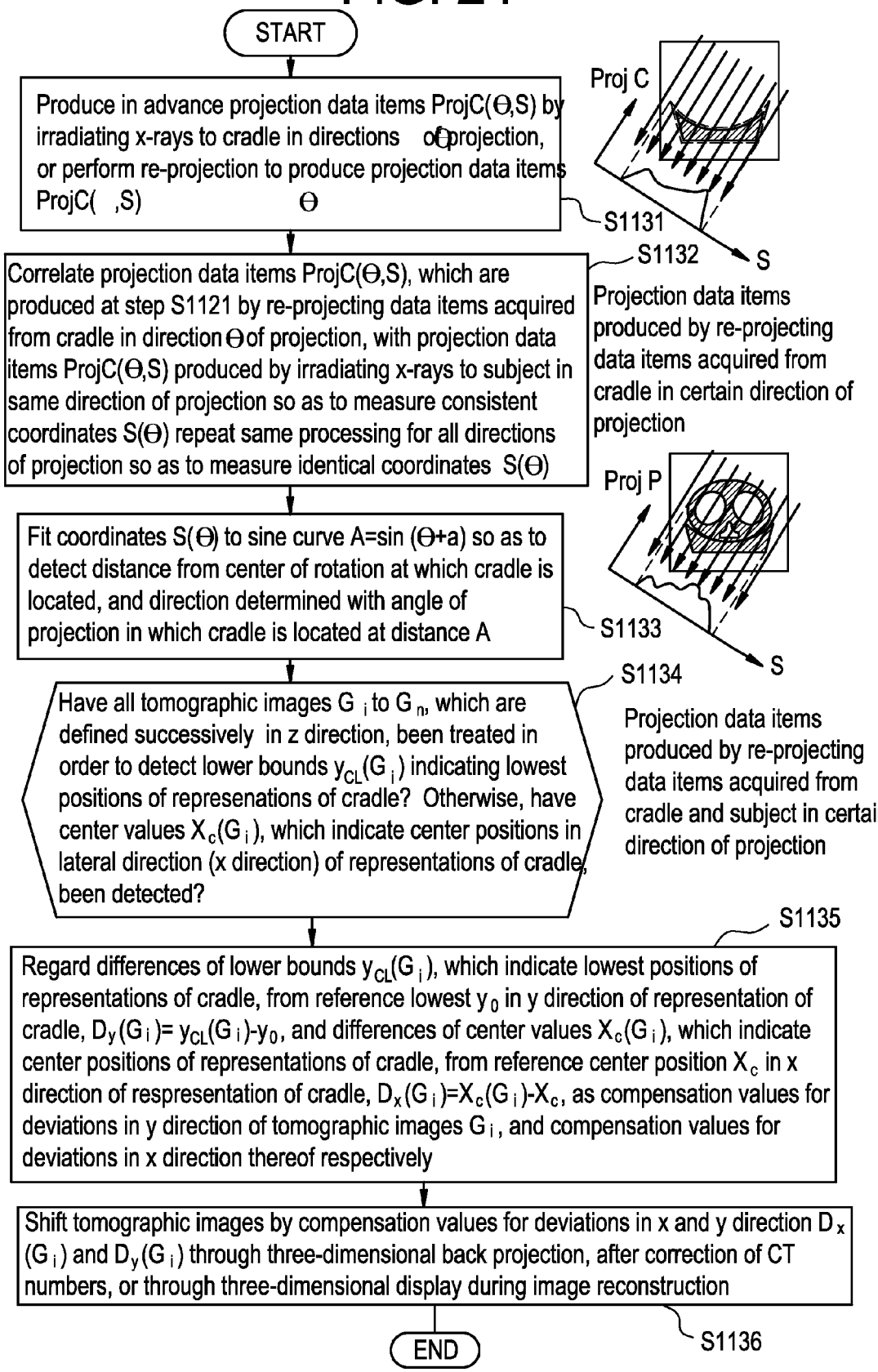

START

S1131: Produce in advance projection data items ProjC(Θ,S) by irradiating x-rays to cradle in directions of projection, or perform re-projection to produce projection data items ProjC( ,S) Θ

Proj C — Projection data items produced by re-projecting data items acquired from cradle in certain direction of projection S1132: Correlate projection data items ProjC(Θ,S), which are produced at step S1121 by re-projecting data items acquired from cradle in direction Θ of projection, with projection data items ProjC(Θ,S) produced by irradiating x-rays to subject in same direction of projection so as to measure consistent coordinates S(Θ) repeat same processing for all directions of projection so as to measure identical coordinates S(Θ)

Proj P — Projection data items produced by re-projecting data items acquired from cradle and subject in certain direction of projection S1133: Fit coordinates S(Θ) to sine curve A=sin (Θ+a) so as to detect distance from center of rotation at which cradle is located, and direction determined with angle of projection in which cradle is located at distance A S1134: Have all tomographic images $G_i$ to $G_n$, which are defined successively in z direction, been treated in order to detect lower bounds $y_{CL}(G_i)$ indicating lowest positions of represenations of cradle? Otherwise, have center values $X_c(G_i)$, which indicate center positions in lateral direction (x direction) of representations of cradle, been detected?

S1135: Regard differences of lower bounds $y_{CL}(G_i)$, which indicate lowest positions of representations of cradle, from reference lowest $y_0$ in y direction of representation of cradle, $D_y(G_i)= y_{CL}(G_i)-y_0$, and differences of center values $X_c(G_i)$, which indicate center positions of representations of cradle, from reference center position $X_c$ in x direction of respresentation of cradle, $D_x(G_i)=X_c(G_i)-X_c$, as compensation values for deviations in y direction of tomographic images $G_i$, and compensation values for deviations in x direction thereof respectively S1136: Shift tomographic images by compensation values for deviations in x and y direction $D_x(G_i)$ and $D_y(G_i)$ through three-dimensional back projection, after correction of CT numbers, or through three-dimensional display during image reconstruction

END

FIG. 25

Locus of coordinates S(Θ) identified with largest values of coordinate among projection data items produced by irradiating X-rays to cradle in directions Θ and registered in advance, projection data items produced by re-projecting data items contained in tomographic images and acquired in directions Θ, and projection data items produced by reprojecting tomographic images

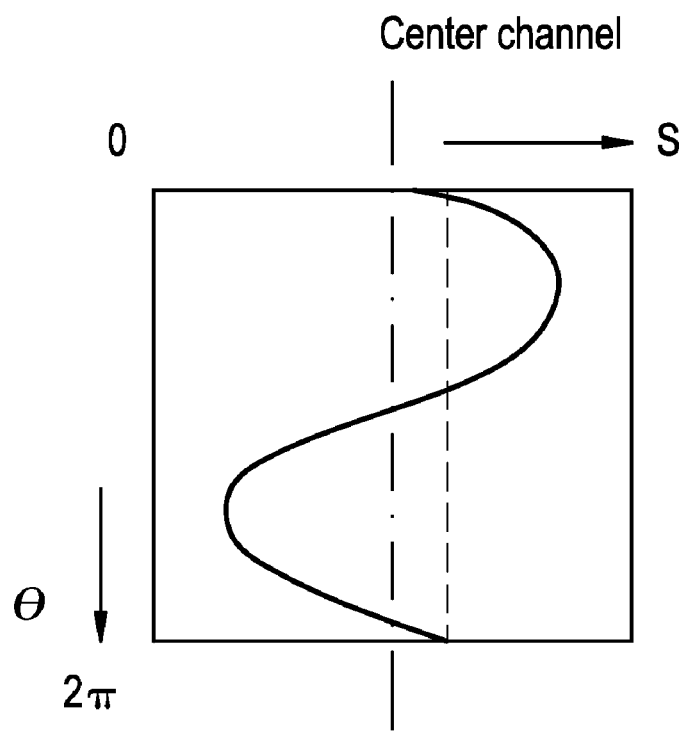

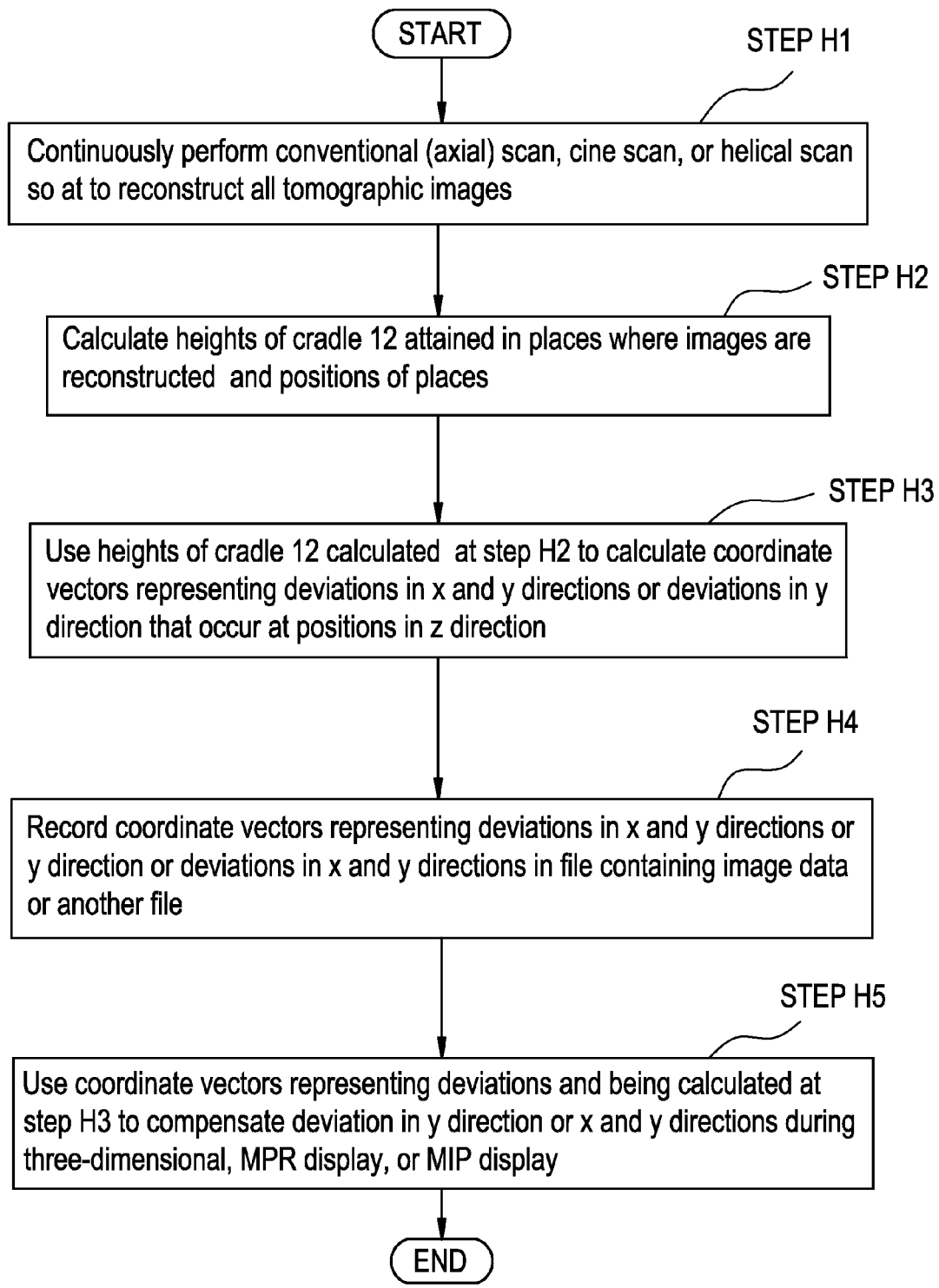

FIG. 26

Example of correcting deviated coordinates, which occur in conventional (axial) scanning, cine scanning, or helical scanning, during image display

START

STEP H1
Continuously perform conventional (axial) scan, cine scan, or helical scan so at to reconstruct all tomographic images

STEP H2
Calculate heights of cradle 12 attained in places where images are reconstructed and positions of places

STEP H3
Use heights of cradle 12 calculated at step H2 to calculate coordinate vectors representing deviations in x and y directions or deviations in y direction that occur at positions in z direction

STEP H4
Record coordinate vectors representing deviations in x and y directions or y direction or deviations in x and y directions in file containing image data or another file

STEP H5
Use coordinate vectors representing deviations and being calculated at step H3 to compensate deviation in y direction or x and y directions during three-dimensional, MPR display, or MIP display

END

Example of correcting deviated coordinates, which occur in helical scanning, during image display while thinning corrected positions Head holder for head Method of producing marginal distribution from projection data items Conversion of slices for conventional (axial) scan or cine scan to be performed with scanner gentry tilted Conversion of slices for helical scan to be performed with scanner gentry tilted

X-RAY CT SYSTEM

CROSS REFERENCE TO RELATED APPLICATIONS

This application claims the benefit of Chinese Application No. 200510118513.3 filed Oct. 27, 2005.

BACKGROUND OF THE INVENTION

The present invention relates to an X-ray computed tomography (CT) system for medical or industrial use, or more particularly, to improvement of quality of a three-dimensional display image, a multi-planar reconstruction (MPR) display image or a maximum intensity projection (MIP) display image.

In X-ray CT systems, an apparatus for generating cone-beam X-rays and a two-dimensional X-ray area detector opposed to the apparatus in order to detect the X-rays and structured with detector elements arranged in the form of a matrix are rotated about a center of rotation located between them. Projection data items produced from X-rays transmitted by a subject lying between the apparatus and the detector are collected, and images are reconstructed based on the collected projection data items. The reconstructed tomographic images are displayed on an image display means (refer to, for example, Patent Document 1).

[Patent Document 1] Japanese Unexamined Patent Publication No. 2003-334188 (pp. 9-10, FIG. 17)

In the X-ray CT system, when a helical scan is performed, the centers of tomographic images are, as shown in FIG. 12, successively deviated from one another along with the movement of a table made in a z direction. Moreover, when a conventional (axial) scan or a cine scan is performed, the centers of tomographic images are, as shown in FIG. 13, deviated from one another on an xy plane, on which the tomographic images are defined, along with the movement of the table made in the z direction. This is attributable to a warp of a cradle, subject's body motions, or the like.

In the past, a slice thickness in the z direction has been large and the dimension of a pixel has not been isotropic. Therefore, when tomographic images are three-dimensionally displayed, the precisions in the positions in x and y directions of each of the tomographic images may not be very high. However, the slice thickness in the z direction has become smaller these days. The dimension of a pixel has become isotropic nowadays. Consequently, as far as a three-dimensional display image, an MPR display image, or an MIP display image is concerned, the deviations of the centers of images on the xy plane pose a problem in terms of accuracy and image quality in that the deviations lead to continuous or discontinuous deviations or steps in the y direction.

However, tomographic images can be aligned on the xy plane using a reference that permits the alignment of the tomographic images on the xy plane, that is, using the continuity of a subject as a reference.

SUMMARY OF THE INVENTION

An object of the present invention is to provide an X-ray CT system capable of improving the quality of a three-dimensional display image, an MPR display image, or an MIP display image produced by performing a conventional (axial) scan, a cine scan, or a helical scan.

The present invention attempts to improve the quality of a three-dimensional display image, an MPR display image, or an MIP display image using an image reconstruction means or an image display means that detects deviations of tomographic images in an x direction that is a horizontal direction or in a y direction that is a vertical direction on the basis of the continuity in an z direction of an object that exhibits high CT numbers, such as; a cradle, a head holder, a subject's body surface, or a subject's bone, and that compensates the deviations. In order to measure the deviations of an image in the x and y directions, a characteristic extraction method, a pattern matching method, a gray-scale pattern matching method, or the like can be adopted.

In the first aspect of the present invention, there is provided an X-ray CT system comprising: an X-ray data collection means that causes an X-ray generator and a two-dimensional X-ray area detector, which is opposed to the X-ray generator in order to detect X-rays and structured with detector elements arranged in the form of a matrix, to rotate about a center of rotation located between them, and that collects projection data items produced from X-rays transmitted by a subject lying between them; an image reconstruction means for reconstructing images according to projection data items collected by the X-ray data collection means; and an image display means for displaying reconstructed tomographic images. Herein, the image display means detects a reference point in each of tomographic images, measures a deviation of each tomographic image in an x direction that is a horizontal direction and a deviation thereof in a y direction that is a vertical direction by measuring the deviations of the reference point, compensates the deviations, and displays resultant tomographic images.

In the X-ray CT system according to the first aspect, a reference point in each of tomographic images is detected according to a characteristic extraction method or a pattern matching method, and deviations of each tomographic image from another are measured. Thus, tomographic images defined successively in a z direction are displayed while being shifted by deviations in x and y directions. The deviations are thus compensated. This results in a three-dimensional display image, an MPR display image, or an MIP display image having the quality thereof improved.

In the second aspect of the present invention, there is provided an X-ray CT system including: an X-ray data collection means that causes an X-ray generator and a two-dimensional X-ray area detector, which is opposed to the X-ray generator in order to detect X-rays and structured with detector elements arranged in the form of a matrix of detector elements, to rotate about a center of rotation between them, and that collects projection data items produced from X-rays transmitted by a subject lying between them; an image reconstruction means that reconstructs images according to projection data items collected by the X-ray data collection means; an image display means that displays reconstructed tomographic images. Herein, the image reconstruction means detects a reference point in each of tomographic images, measures a deviation of each tomographic image in an x direction that is a horizontal direction and a deviation thereof in a y direction that is a vertical direction by measuring the deviations of the reference point, compensates the deviations, and reconstructs resultant tomographic images.

In the X-ray CT system according to the second aspect, a reference point in each of tomographic images is detected according to a characteristic extraction method or a pattern matching method. Deviations of each tomographic image from another are measured. Each of tomographic images defined successively in a z direction is shifted by the deviations in x and y directions for image reconstruction. Thus, the deviations are compensated. This results in a three-dimensional display image, an MPR display image, or an MIP display image having the quality thereof improved.

In the third aspect of the present invention, there is provided an X-ray CT system identical to the X-ray CT system according to the first or second aspect except that the two-dimensional area detector included in the X-ray data collection means is a multi-array X-ray detector.

In the X-ray CT system according to the third aspect, although the two-dimensional X-ray area detector is a multi-array X-ray detector, a three-dimensional display image, an MPR display image, or an MIP display image having the quality thereof improved is produced.

In the fourth aspect of the present invention, there is provided an X-ray CT system identical to the X-ray CT system according to the first or second aspect except that the two-dimensional X-ray area detector included in the X-ray data collection means is a flat X-ray detector represented by a flat-panel X-ray detector.

In the X-ray CT system according to the fourth aspect, although the two-dimensional X-ray area detector is a flat X-ray detector represented by a flat-panel X-ray detector, a three-dimensional display image, an MPR display image, or an MIP display image having the quality thereof improved is produced.

In the fifth aspect of the present invention, there is provided an X-ray CT system identical to the X-ray CT system according to any of the first to fourth aspects except that: the image display means detects a reference point in each of tomographic images that are produced by continuously performing a helical scan in a z direction perpendicular to an xy plane on which the tomographic images are defined; the image display means then measures a deviation of each tomographic image in an x direction that is a horizontal direction and a deviation thereof in a y direction that is a vertical direction by measuring the deviations of the reference point; and the image display means compensates the deviations and displays resultant tomographic images.

In the X-ray CT system according to the fifth aspect, the deviations in the x and y directions of each of tomographic images produced by continuously performing a helical scan in the z direction, that is, each of tomographic images defined to lie at positions indicated with z-coordinates are measured, and the tomographic images are displayed while being shifted by the deviations in the x and y directions. This results in a three-dimensional display image, an MPR display image, or an MIP display image having the quality thereof improved.

In the sixth aspect of the present invention, there is provided an X-ray CT system identical to the X-ray CT system according to any of the first to fourth aspects except that: the image reconstruction means detects a reference point in each of tomographic images that are produced by continuously performing a helical scan in a z direction perpendicular to an xy plane on which the tomographic images are defined; the image reconstruction means measures a deviation of each tomographic image in an x direction that is a horizontal direction and a deviation thereof in a y direction that is a vertical direction by measuring the deviations of the reference point; and the image reconstruction means compensates the deviations, and reconstructs resultant tomographic images.

In the X-ray CT system according to the sixth aspect, the deviations in the x and y directions of each of tomographic images produced by continuously performing a helical scan in the z direction, that is, each of tomographic images defined to lie at positions indicated with z-coordinates are measured, and the tomographic images are shifted by the deviations in the x and y directions and then reconstructed. This results in a three-dimensional display image, an MPR display image, or an MIP display image having the quality thereof improved.

In the seventh aspect of the present invention, there is provided an X-ray CT system identical to the X-ray CT system according to any of the first to fourth aspects except that: the image display means detects a reference point in each of tomographic images that are produced by continuously performing a conventional (axial) scan in a z direction perpendicular to an xy plane on which the tomographic images are defined; the image display means measures a deviation of each tomographic image in an x direction that is a horizontal direction and a deviation thereof in a y direction that is a vertical direction; and the image display means compensates the deviations and displays resultant tomographic images.

In the X-ray CT system according to the seventh aspect, the deviations in the x and y directions of each of tomographic images produced by continuously performing a conventional (axial) scan in the z direction are measured during each scan. Otherwise, the deviations in the x and y directions of each of tomographic images defined to lie at positions indicated with z-coordinates are measured. The tomographic images are displayed while being shifted by the deviations in the x and y directions. This results in a three-dimensional display image, an MPR display image, or an MIP display image having the quality thereof improved.

In the eighth aspect of the present invention, there is provided an X-ray CT system identical to the X-ray CT system according to any of the first to fourth aspects except that: the image reconstruction means detects a reference point in each of tomographic images that are produced by continuously performing a conventional (axial) scan in a z direction perpendicular to an xy plane on which the tomographic images are defined; the image reconstruction means measures a deviations of each tomographic image in an x direction that is a horizontal direction and a deviation thereof in a y direction that is a vertical direction by measuring the deviations of the reference points; and the image reconstruction means compensates the deviations and reconstructs resultant tomographic images.

In the X-ray CT system according to the eight aspect, the deviations in the x and y directions of each of tomographic images produced by continuously performing a conventional (axial) scan in the z direction are measured during each scan. Otherwise, the deviations in the x and y direction of each of tomographic images defined to lie at positions indicated with z-coordinates are measured. The tomographic images are shifted by the deviations in the x and y directions and then reconstructed. This results in a three-dimensional display image, an MPR display image, or an MIP display image having the quality thereof improved.

In the ninth aspect of the present invention, there is provided an X-ray CT system identical to the X-ray CT system according to any of the first to fourth aspects except that: the image display means detects a reference point in each of tomographic images that are produced by continuously performing a cine scan in a z direction perpendicular to an xy plane on which the tomographic images are defined; the image display means measures a deviations of each tomographic image in an x direction that is a horizontal direction and a deviation thereof in a y direction that is a vertical direction by measuring the deviations of the reference point; and the image display means compensates the deviations and displays resultant tomographic images.

In the X-ray CT system according to the ninth aspect, the deviations in the x and y directions of each of tomographic images produced by continuously performing a cine scan in the z direction are measured during each scan. Otherwise, the deviations in the x and y directions of each of tomographic images defined to lie at positions indicated with z-coordinates are measured. The tomographic images are displayed while being shifted by the deviations in the x and y directions. This results in a three-dimensional display image, an MPR display image, or an MIP display image having the quality thereof improved.

In the tenth aspect of the present invention, there is provided an X-ray CT system identical to the X-ray CT system according to any of the first to fourth aspects except that: the image reconstruction means detects a reference point in each of tomographic images that are produced by continuously performing a cine scan in a z direction perpendicular to an xy plane on which the tomographic images are defined; the image reconstruction means measures a deviation of each tomographic image in an x direction that is a horizontal direction and a deviation thereof in a y direction that is a vertical direction by measuring the deviations of the reference point; and the image reconstruction means compensates the deviations and reconstructs resultant tomographic images.

In the X-ray CT system according to the tenth aspect, the deviations in the x and y directions of each of tomographic images produced by continuously performing a cine scan in the z direction are measured during each scan. Otherwise, the deviations in the x and y directions of each of tomographic images defined to lie at positions indicated with z-coordinates are measured. The tomographic images are shifted by the deviations in the x and y directions and then reconstructed. This results in a three-dimensional display image, an MPR display image, or an MIP display image having the quality thereof improved.

In the eleventh aspect of the present invention, there is provided an X-ray CT system identical to the X-ray CT system according to any of the first to fourth aspects except that: the image display means detects a reference point in each of tomographic images that are produced by continuously performing a variable-pitch helical scan in a z direction perpendicular to an xy plane on which the tomographic images are defined; the image display means measures a deviation of each tomographic image in an x direction that is a horizontal direction and a deviation thereof in a y direction that is a vertical direction by measuring the deviations of the reference point; and the image display means compensates the deviations and displays resultant tomographic image.

In the X-ray CT system according to the eleventh aspect, the deviations in the x and y directions of each of tomographic images produced by continuously performing a variable-pitch helical scan in the z direction or tomographic images located at positions indicated with z-coordinates are measured. The tomographic images are displayed while being shifted by the deviations in the x and y directions. This results in a three-dimensional display image, an MPR display image, or an MIP display image having the quality thereof improved.

In the twelfth aspect of the present invention, there is provided an X-ray CT system identical to the X-ray CT system according to any of the first to fourth aspects except that: the image reconstruction means detects a reference point in each of tomographic images that are produced by continuously performing a variable-pitch helical scan in a z direction perpendicular to an xy plane on which the tomographic images are defined; the image reconstruction image measures a deviation of each tomographic image in an x direction that is a horizontal direction and a deviation thereof in a y direction that is a vertical direction by measuring the deviations of the reference point; and the image reconstruction means compensates the deviations and reconstructs resultant tomographic images.

In the X-ray CT system according to the twelfth aspect, the deviations in the x and y directions of each of tomographic images produced by continuously performing a variable-pitch helical scan in the z direction or tomographic images defined to lie at positions indicated with z-coordinates are measured. The tomographic images are shifted by the deviations in the x and y directions for image reconstruction. This results in a three-dimensional display image, an MPR display image, or an MIP display image having the quality thereof improved.

In the thirteenth aspect of the present invention, there is provided an X-ray CT system identical to the X-ray CT system according to any of the first to twelfth aspects except that the image display means uses a representation of part of a cradle as a reference point in each of tomographic images to compensate deviations, and then displays resultant tomographic images.

In the X-ray CT system according to the thirteenth aspect, a representation of part of a cradle is used as a reference point in each of tomographic images to measure the deviations in the x and y directions of each tomographic image. The tomographic images are displayed while being shifted by the deviations in the x and y directions. This results in a three-dimensional display image, an MPR display image, or an MIP display image having the quality thereof improved.

In the fourteenth aspect of the present invention, there is provided an X-ray CT system identical to the X-ray CT system according to any of the first to twelfth aspects except that the image reconstruction means uses a representation of part of a cradle as a reference point in each of tomographic images, compensates the deviations, and reconstructs resultant tomographic images.

In the X-ray CT system according to the fourteenth aspect, a representation of part of a cradle is detected as a reference point in each of tomographic images, and the deviations in the x and y directions of each of the tomographic image are measured. The tomographic images are shifted by the deviations in the x and y directions and then reconstructed. This results in a three-dimensional display image, an MPR display image, or an MIP display image having the quality thereof improved.

In the fifteenth aspect of the present invention, there is provided an X-ray CT system identical to the X-ray CT system according to any of the first to twelfth aspects except that the image display means uses a representation of part of a subject as a reference point in each of tomographic images and displays resultant tomographic images.

In the X-ray CT system according to the fifteenth aspect, a representation of part of a subject is detected as a reference point in each of tomographic images, and the deviations in the x and y directions of each tomographic image are measured. The tomographic images are displayed while being shifted by the deviations in the x and y directions. This results in a three-dimensional display image, an MPR display image, or an MIP display image having the quality thereof improved.

In the sixteenth aspect of the present invention, there is provided an X-ray CT system identical to the X-ray CT system according to any of the first to twelfth aspects except that the image reconstruction means uses a representation of part of a subject as a reference point in each of tomographic images to reconstruct tomographic images.

In the X-ray CT system according to the sixteenth aspect, a representation of part of a subject is detected as a reference point in each of tomographic images, and the deviations in the x and y directions of each tomographic image are measured. The tomographic images are shifted by the deviations in the x and y directions and then reconstructed. This results in a three-dimensional display image, an MPR display image, or an MIP display image having the quality thereof improved.

In the seventeenth aspect of the present invention, there is provided an X-ray CT system identical to the X-ray CT system according to any of the first to sixteenth aspects except that the image reconstruction means adopts a three-dimensional image reconstruction technique. In the X-ray CT system according to the seventeenth aspect, although the three-dimensional image reconstruction technique is adopted as a technique of image reconstruction, a three-dimensional display image, an MPR display image, or an MIP display image having the quality thereof improved is produced.

In the eighteenth aspect of the present invention, there is provided an X-ray CT system identical to the X-ray CT system according to any of the first to seventeenth aspects except that the image display means compensates not only the deviations in the x and y directions of tomographic images but also the deviation in the z direction thereof, and displays the resultant tomographic images.

In the X-ray CT system according to the eighteenth aspect, although not only the deviations in the x and y directions of tomographic images but also the deviation in the z direction thereof are compensated in order to display resultant tomographic images, a three-dimensional display image, an MPR display image, or an MIP display image having the quality thereof improved is produced.

In the nineteenth aspect of the present invention, there is provided an X-ray CT system identical to the X-ray CT system according to any of the first to seventeenth aspects except that the image reconstruction means compensates not only the deviations in the x and y directions of tomographic images but also the deviation in the z direction thereof and reconstructs resultant tomographic images.

In the X-ray CT system according to the nineteenth aspect, although not only the deviations in the x and y directions of tomographic images but also the deviation in the z direction thereof are compensated in order to reconstruct resultant images, a three-dimensional display image, an MPR display image, or an MIP display image having the quality thereof improved is produced.

An X-ray CT system according to the present invention makes it possible to improve the quality of a three-dimensional display image, an MPR display image, or an MIP display image produced by performing conventional (axial) scans, cine scans, or helical scans.

Further objects and advantages of the present invention will be apparent from the following description of the preferred embodiments of the invention as illustrated in the accompanying drawings.

BRIEF DESCRIPTION OF THE DRAWINGS

FIG. 7 is a conceptual diagram showing lines projected onto the surface of a detector.

FIG. 8 is a conceptual diagram showing projection of projection data items Dr(view,x,y) onto a scan field.

FIG. 9 is a conceptual diagram showing back projection pixel data items D2 serving as pixels in the scan field.

FIG. 10 is an explanatory diagram showing production of back projection data items D3 by adding up pixel by pixel back projection pixel data items D2 produced from all views.

FIG. 13 shows deviations of the centers of tomographic images, which are produced by performing an axial scan, observed in a conventional three-dimensional display image, MPR display image, or MIP display image.

FIG. 14 shows a conventional (axial) scan or a cine scan continuously performed in a z direction.

FIG. 15 shows a conventional (axial) scan or a cine scan continuously performed in the z direction.

FIG. 16 shows a conventional (axial) scan or a cine scan continuously performed in the z direction.

FIG. 17 shows deviations in a y direction of tomographic images defined successively in the z direction.

FIG. 18 describes compensation of deviations in the y direction according to a method of extracting characteristic parameters through marginal distribution measurement.

FIG. 19 describes compensation of deviations in the x and y directions according to a method of extracting characteristic parameters through characteristic parameter measurement.

FIG. 21 shows a logical filter for expansion.

FIG. 22 shows a logical filter for contraction.

FIG. 24 shows a method of correcting deviated x- and y-coordinates according to a method of matching projection data items with a cradle pattern.

FIG. 25 shows a locus of coordinates S(θ) identified with the largest values of correlation among projection data items produced by irradiating X-rays to the cradle in directions θ and registered in advance, projection data items produced by re-projecting data items contained in tomographic images and acquired in the directions θ, and projection data items produced by re-projecting tomographic images.

FIG. 26 describes an example of correcting deviated coordinates, which are derived from a continuous conventional (axial) scan, cine scan, or helical scan, during image display.

DETAILED DESCRIPTION OF THE INVENTION

The present invention will be described below by taking an illustrated embodiment for instance. Noted is that the present invention will not be limited to the embodiment.

Figure 1:
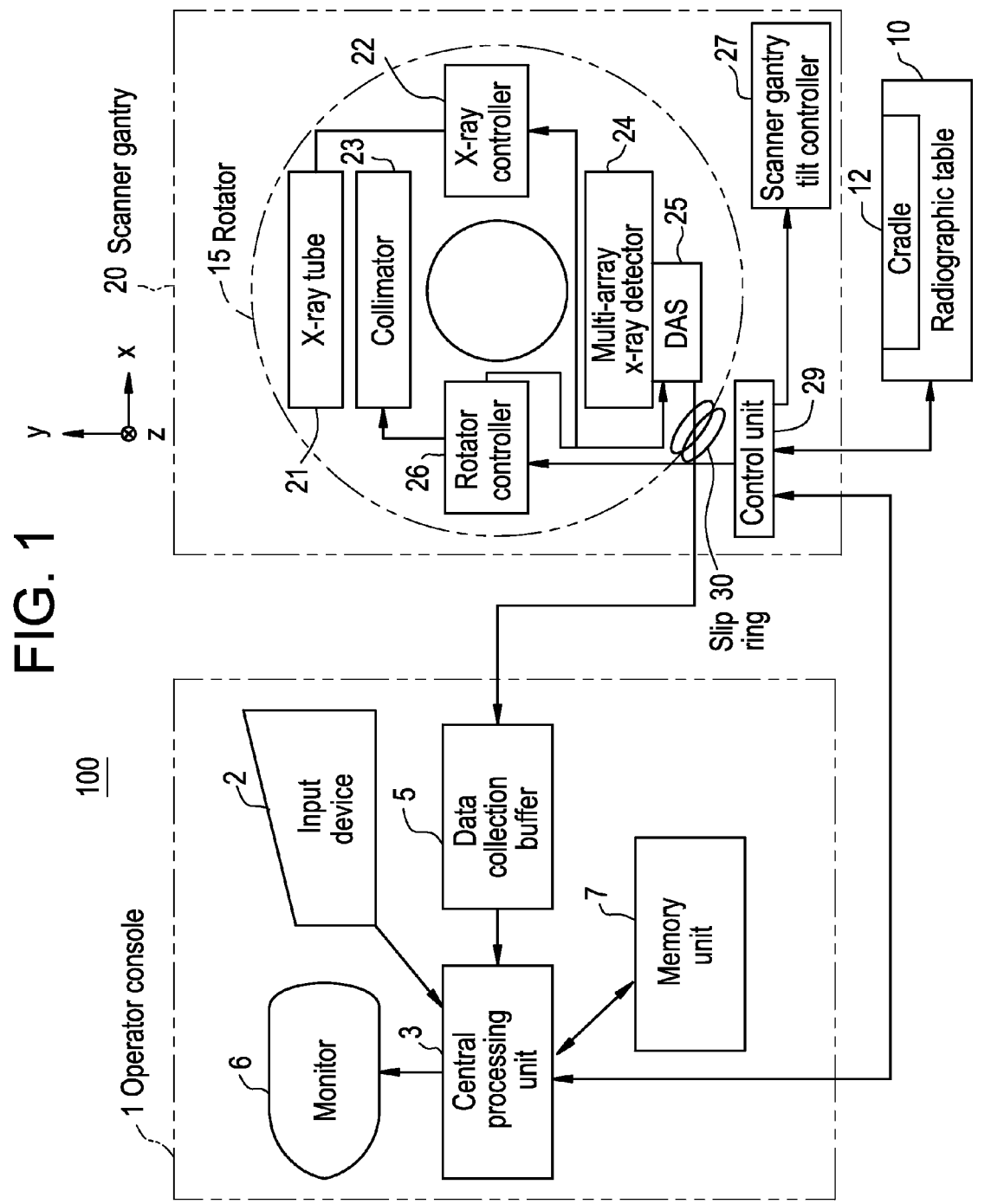
FIG. 1 is a block diagram showing an X-ray CT system in accordance with an example of the best mode for implementing the present invention.

FIG. 1 is a block diagram showing the configuration of an X-ray CT system in accordance with the best mode for implementing the present invention. An X-ray CT system 100 includes an operator console 1, a radiographic table 10, and a scanner gantry 20.

The operator console 1 includes an input device 2 that receives an operator's input, a central processing unit 3 that performs preprocessing, image reconstruction, and post-processing, a data collection buffer 5 that collects X-ray detector data items, that is, data items acquired by an X-ray detector included in the scanner gantry 20, a monitor 6 on which tomographic images reconstructed based on projection data items produced by performing preprocessing on the X-ray detector data items, and a memory unit 7 in which programs, the X-ray detector data items, the projection data items, and X-ray tomographic images are stored.

The radiographic table 10 includes a cradle 12 that carries a subject, who lies down thereon, into or out of the bore of the scanner gantry 20. The cradle 12 is lifted or lowered by a motor incorporated in the radiographic table 10 and moved rectilinearly with respect to the table 10.

The scanner gantry 20 includes an X-ray tube 21, an X-ray controller 22, a collimator 23, a multi-array X-ray detector 24, a data acquisition system (DAS) 25, a rotator controller 26 that controls the X-ray tube 21 and others which rotate about a subject's body axis, and a control unit 29 that transfers control signals and others to or from the operator console 1 or the radiographic table 10. Moreover, a scanner gantry tilt controller 27 tilts the scanner gantry 20 forward or backward at approximately ±30°.

Figure 2:
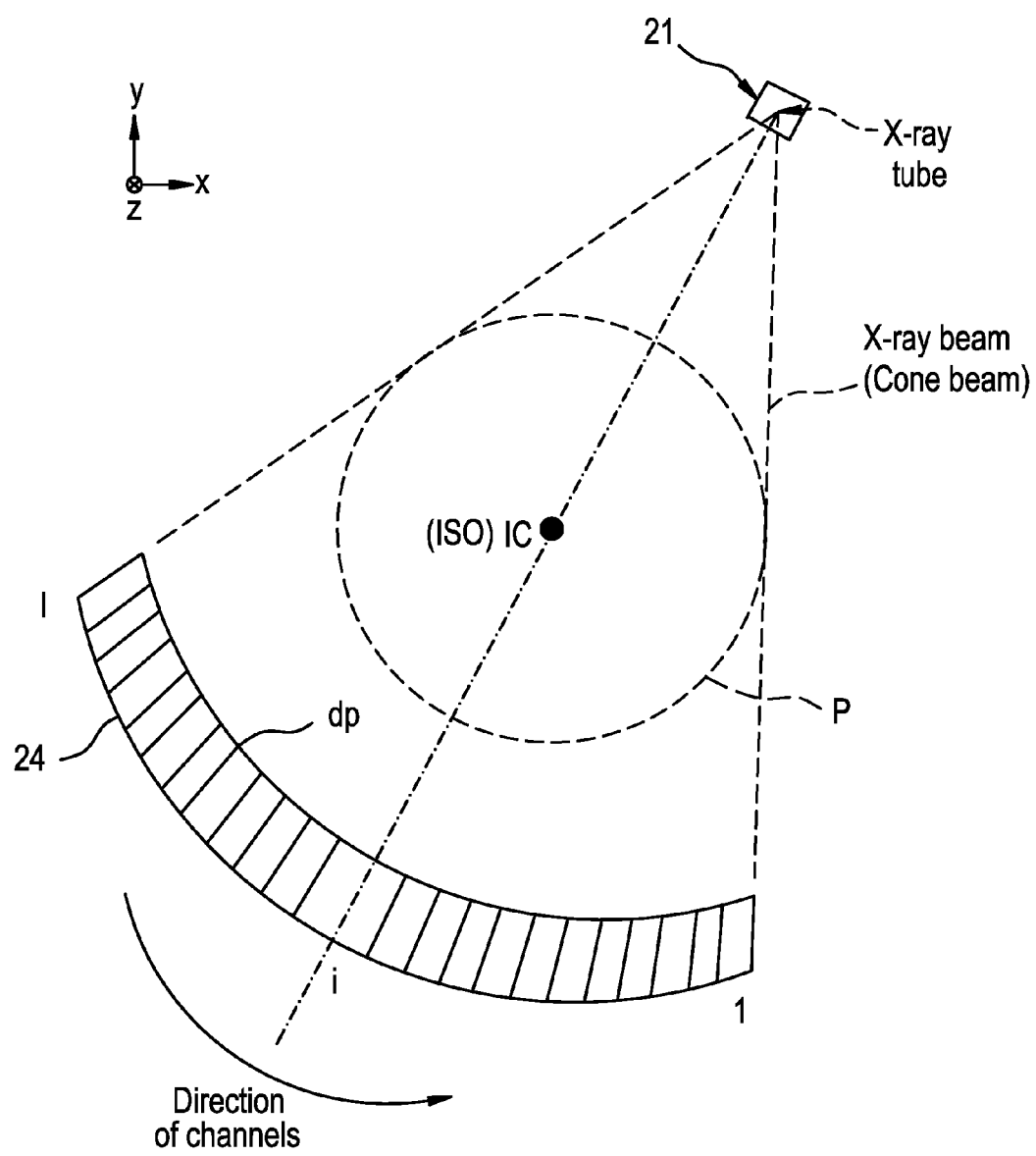
FIG. 2 is an explanatory diagram showing rotations of an X-ray generator (X-ray tube) and a multi-array X-ray detector.

FIG. 2 is an explanatory diagram showing the geometric disposition of the X-ray tube 21 and the multi-array X-ray detector 24.

The X-ray tube 21 and the multi-array X-ray detector 24 rotate about a center of rotation IC. Assuming that a vertical direction is a y direction, a horizontal direction is an x direction, and a direction of advancement of the table perpendicular to the x and y directions is a z direction, the plane of rotation on which the X-ray tube 21 and the multi-array X-ray detector 24 rotate is an xy plane. The direction of movement of the cradle 12 is the z direction.

The X-ray tube 21 generates an X-ray beam called a cone beam. When the direction of the center axis of the cone beam is parallel to the y direction, it says that a view angle or the angle of the scanner gantry is 0°.

The multi-array X-ray detector 24 includes, for example, 256 detector arrays. Each of the detector arrays includes, for example, 1024 detector channels.

After X-rays are irradiated, projection data is produced and collected. The projection data produced by the multi-array X-ray detector 24 is analog-to-digital converted by the DAS 25, and transferred to the data collection buffer 5 via a slip ring 30. The data transferred to the data collection buffer 5 is processed by the central processing unit 3 according to a program read from the memory unit 7. A tomographic image is reconstructed according to the processed data, and then displayed on the monitor 6.

Figure 3:
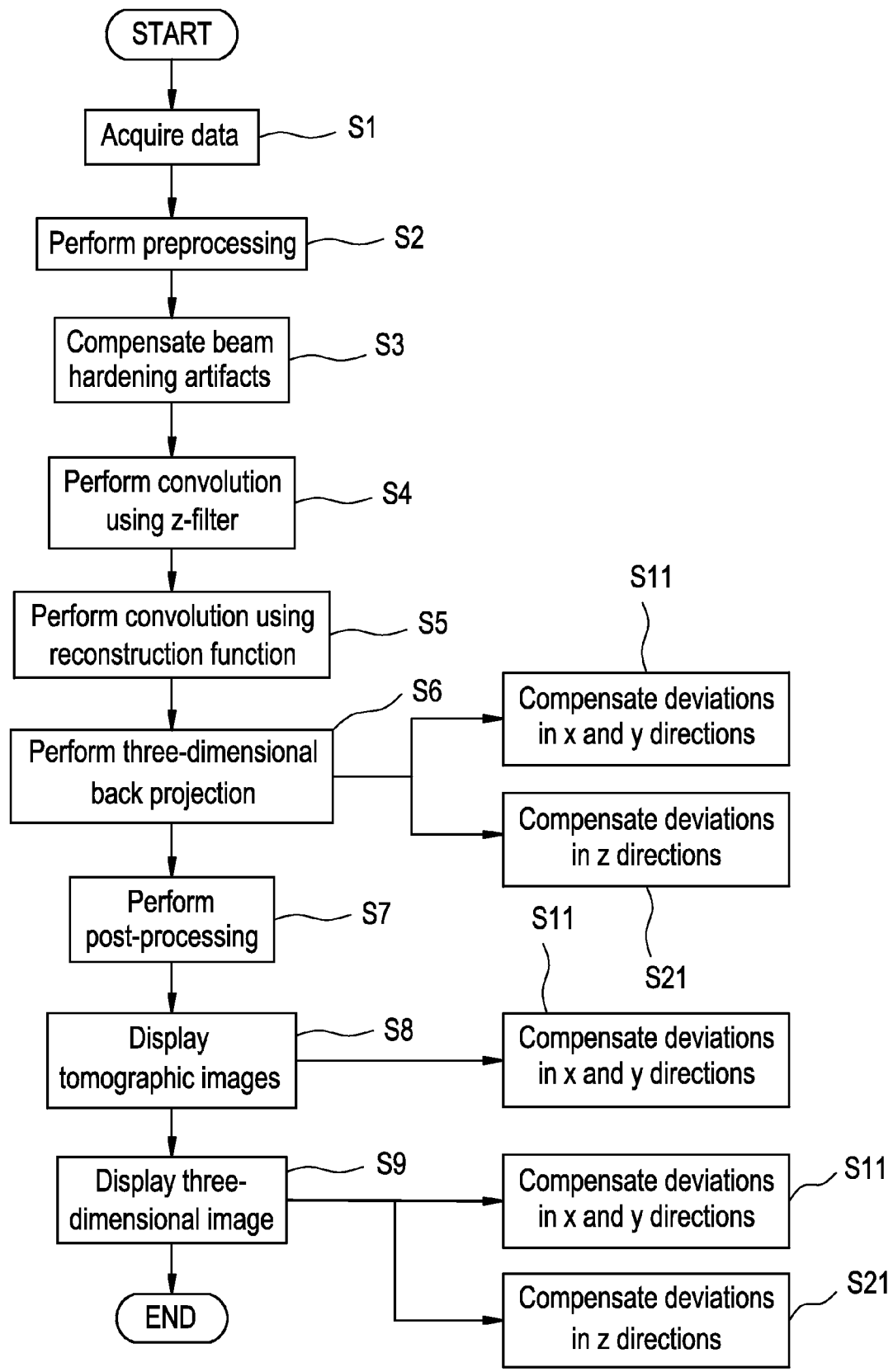
FIG. 3 is a flowchart outlining the actions to be performed in the X-ray CT system in accordance with the example of the best mode for implementing the present invention.

Scanning techniques employed in the present invention include conventional (axial) scanning, cine scanning, and helical scanning. The scanning techniques will be described in relation to the first and second examples later. FIG. 3 is a flowchart outlining actions to be performed in the X-ray CT system 100 in accordance with the present invention.

At step S1, first, the X-ray tube 21 and the multi-array X-ray detector 24 are rotated about a subject and the cradle 12 included in the radiographic table is rectilinearly moved in order to continuously perform a helical scan or a variable-pitch helical scan. Data items acquired by the X-ray detector, that is, X-ray detector data items DO(view,j,i) each identified with a view angle view, a detector array number j, and a channel number i are collected with a position Ztable(view) in the z direction, in which the table is rectilinearly moved, appended to each X-ray detector data.

For conventional (axial) scanning or cine scanning, the cradle 12 included in the radiographic table 10 is moved in units of a length equal to or smaller than the width D on the z axis of an X-ray beam having passed through the center of rotation. A conventional (axial) scan or cine scan is then continuously performed in the z direction in order to collect X-ray detector data items DO(view,j,i) each identified with a view angle view, a detector array number j, and a channel number I with a position Ztable(view) in the z direction, in which the table is rectilinearly moved, appended to each X-ray detector data.

At step S2, X-ray detector data items D0(view,j,i) are preprocessed and converted into projection data items. The preprocessing includes, as described in FIG. 4, offset nulling of step S21, logarithmic conversion of step S22, X-ray dose correction of step S23, and sensitivity correction of step S24.

At step S3, beam hardening artifacts contained in each of the preprocessed projection data items D1(view,j,i) are compensated. During the beam hardening compensation of step S3, assuming that projection data having undergone sensitivity correction of step S24 included in the preprocessing of step S2 is data Din and data having beam hardening artifacts compensated at step S3 is data Dout, the beam hardening compensation of step S3 is expressed by the following polynomial:

$$Dout(view,j,i) = Din(view,j,i) \cdot (B_0(j,i) + B_1(j,i) \cdot Din(view,j,i) + B_2(j,i) \cdot Din(view,j,i)^2) \quad \text{[Formula 1]}$$

At this time, the beam hardening compensation is performed on projection data produced by each detector array j. If the tube current is specified as one of radiographic conditions differently among data collection systems, the differences among the X-ray photon energy characteristics of detector elements belonging to each detector array can be compensated.

At step S4, the projection data items Dout(view,j,i) having undergone the beam hardening compensation are convoluted using a z-filter, that is, the projection data items Dout(view,j,i) are filtered in the z direction (direction of arrays).

At step S4, a z-filter capable of treating projection data items produced by five detector elements juxtaposed in the direction of arrays is applied to projection data items that are produced by the multi-array X-ray detector Det(ch,row) (ch ranges from 1 to CH and row ranges from 1 to ROW) at each view angle and that are preprocessed by the respective data collection systems. The filter is expressed as follows:

$$(w_1(ch), w_2(ch), w_3(ch), w_4(ch), w_5(ch))$$

Herein, the condition provided by the formula below shall be met.

$$\sum_{k=1}^{5} w_k(ch) = 1 \qquad \text{[Formula 2]}$$

The corrected detector data items Dcor(ch,row) are expressed as follows:

$$Dcor(ch, j) = \sum_{k=1}^{5} (Det(ch, i-k-3) \cdot w_k(ch)) \qquad \text{[Formula 3]}$$

Assuming that the largest channel number is CH and the largest array number is ROW, the following relationships are established:

Det(ch,−1)=Det(ch,0)=Det(ch,1)

Det(ch,ROW)=Det(ch,ROW+1)=Det(ch,ROW+2)　　[Formula 4]

When filtering coefficients to be applied to projection data items produced by five detector elements juxtaposed in the direction of arrays are changed channel by channel, a slice thickness can be controlled according to a distance from the center of a scan field that is a field of a reconstructed image. In general, the slice thickness to be covered by a tomographic image is larger in the perimeter of the scan field than in the center thereof. The filtering coefficients to be applied to projection data items produced by five detector elements juxtaposed in the direction of arrays are changed largely for detector elements belonging to central channels, and changed slightly for detector elements belonging to peripheral channels. In this case, the slice thickness becomes equal between the perimeter of the scan field and the center thereof.

Since the filtering coefficients to be applied to projection data items produced by detector elements belonging to central channels of the multi-array X-ray detector 24 or detector elements belonging to peripheral channels thereof are controlled as mentioned above, the slice thickness can be controlled according to whether it is concerned with the center of a scan field or with the perimeter thereof. When the filtering coefficients to be applied to projection data items produced by detector elements juxtaposed in the direction of arrays are used to increase a slice thickness a bit, artifacts and noises can be canceled satisfactorily. Thus, the degree to which artifacts or noises are canceled can be controlled. Namely, the quality of a three-dimensionally reconstructed tomographic image, that is, the image quality on an xy plane can be controlled. In a variant, the filtering coefficients to be applied to projection data items produced by detector elements juxtaposed in the direction of arrays (z direction) are determined to realize de-convolution, whereby a tomographic image covering a small slice thickness can be reconstructed.

At step S5, convolution is performed using a reconstruction function. Specifically, Fourier transform is performed, a reconstruction function is applied, and inverse Fourier transform is then performed. During the reconstruction function convolution of step S5, assuming that data having been convoluted using the z-filter is data Din, data having been convoluted using the reconstruction function is data Dout, and the reconstruction function used for convolution is a function Kernel(j), the reconstruction function convolution is expressed as follows:

$$Dout(view,j,i) = Din(view,j,i) * Kernel(j) \qquad \text{[Formula 5]}$$

Since the reconstruction function Kernel(j) permits reconstruction function convolution to be independently performed on each of the detector arrays j, the differences in a noise characteristic and a resolution characteristic among the detector elements belonging to each detector array can be compensated.

At step S6, three-dimensional back projection is performed on projection data items D0(view,j,i) having been convoluted using the reconstruction function in order to produce back projection data items D33(x,y). Images are three-dimensionally reconstructed on a plane defined to be perpendicular to the z axis, that is, an xy plane. Hereinafter, a scan field P shall be parallel to the xy plane. Three-dimensional back projection will be described later with reference to FIG. 5. Compensation of deviations in the x and y directions of step 11 that will be described later may be performed on tomographic images resulting from the three-dimensional back projection. Furthermore, three-dimensional back projection may be performed in consideration of deviations in the z direction that are compensated at step 12.

At step S7, post-processing including image filter convolution and CT number conversion is performed on back projection data items D3(x,y) in order to complete tomographic images. Compensation of deviations in the x and y directions of step S11 that will be described later may be performed on the tomographic images having CT numbers thereof converted.

During image filter convolution that is included in post-processing, assuming that data having undergone three-dimensional back projection is data Din(x,y,z), data having undergone image filter convolution is data Dout(x,y,z), and an image filter is a filter Filter(z), the image filter convolution is expressed as follows:

$$Dout(x,y,z) = Din(x,y,z) * Filter(z) \qquad \text{[Formula 6]}$$

Since image filter convolution can be independently performed on each of the detector arrays j, the differences in a noise characteristic and a resolution characteristic among the detector elements belonging to each array can be compensated.

At step S8, the resultant tomographic images are displayed on the monitor 6.

At step S9, tomographic images produced by continuously performing the conventional (axial) scan, cine scan, helical scan, or variable-pitch helical scan so as to be defined successively in the z direction are displayed according to a three-dimensional image display technique, an MPR image display technique, or an MIP image display technique.

For the three-dimensional image display, compensation of deviations in the x and y directions that will be described later may be performed. Furthermore, deviations in the z direction may be compensated for the three-dimensional display.

Figure 4:
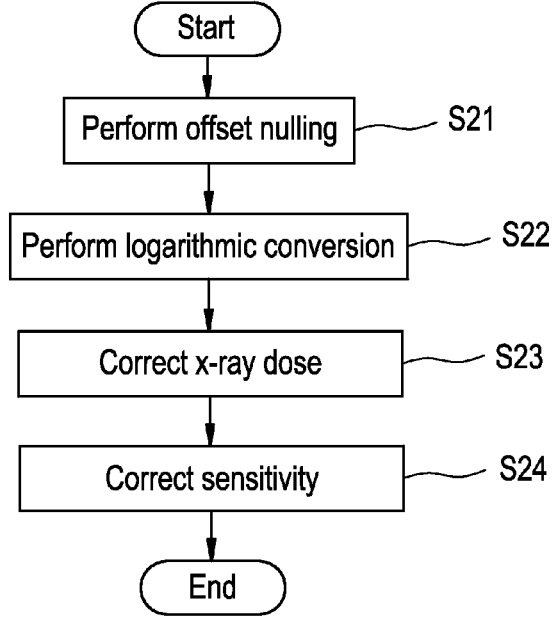
FIG. 4 is a flowchart describing pre-processing.
Figure 5:
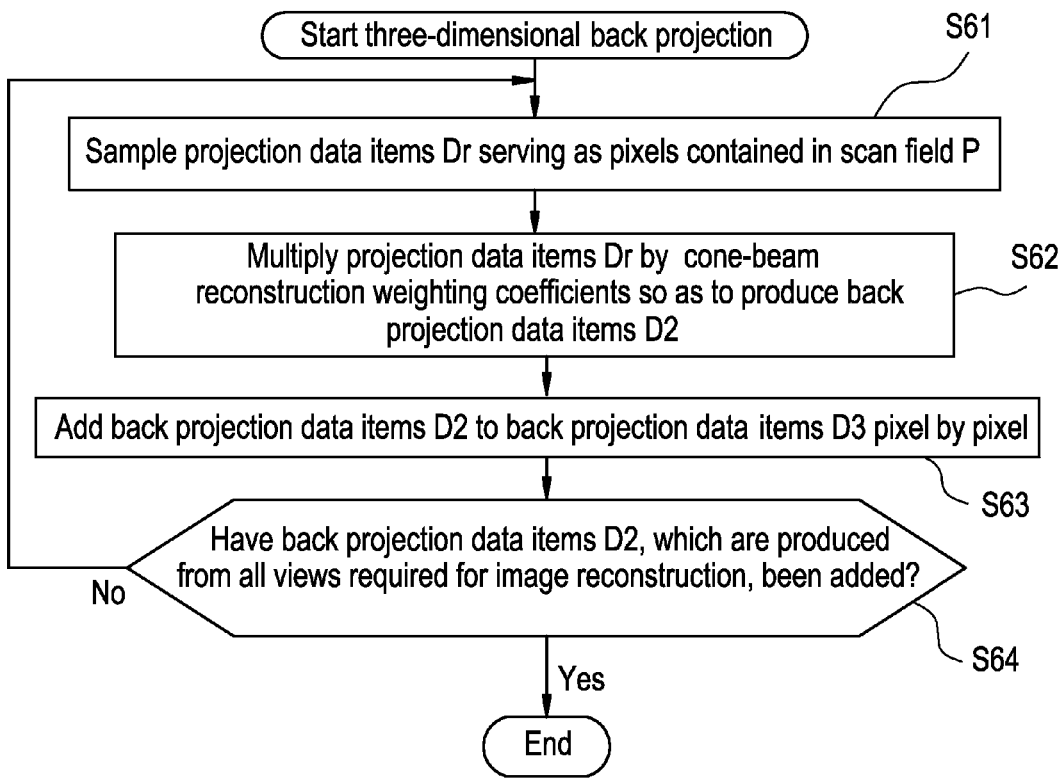
FIG. 5 is a flowchart describing three-dimensional image reconstruction.

FIG. 5 is a flowchart describing three-dimensional back projection (step S6 in FIG. 4).

According to the present invention, the helical scanning is adopted. Images are three-dimensionally reconstructed on a plane defined to be perpendicular to the z axis, that is, an xy plane. Hereinafter, a scan field P shall be parallel to the xy plane.

At step S61, projection data items Dr serving as pixels contained in the scan field P are sampled as one of all views required for reconstruction of tomographic images (that is, views covering 360° or views covering the sum of 180° and an angle of a fan-shaped beam).

Figure 6A:
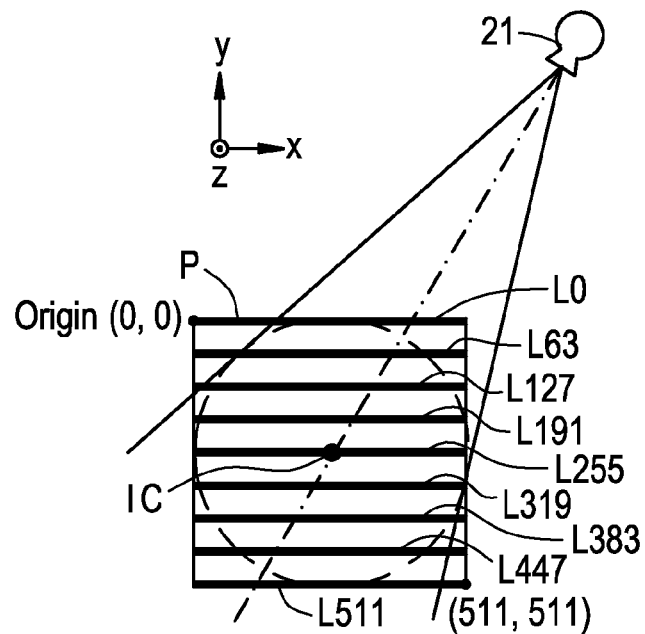
FIGS. 6a and 6b are conceptual diagrams showing projection of lines in a scan field in a direction of X-ray transmission.
Figure 6B:
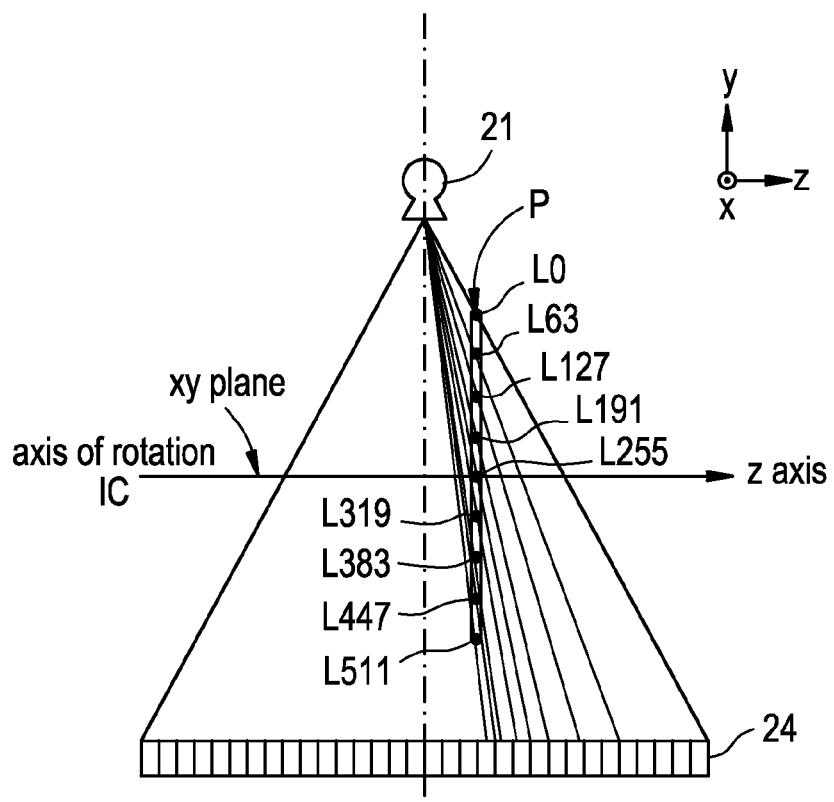

As shown in FIG. 6(a) and FIG. 6(b), the scan field P shall be a square domain containing 512 pixels in rows and columns and being parallel to the xy plane. A row L0 of pixels starting at a y-coordinate 0 and being parallel to the x axis, a row L63 of pixels starting at a y-coordinate 63, a row L127 of pixels starting at a y-coordinate 127, a row L191 of pixels starting at a y-coordinate 191, a row L255 of pixels starting at a y-coordinate 255, a row L319 of pixels starting at a y-coordinate 319, a row L383 of pixels starting at a y-coordinate 383, a row L447 of pixels starting at a y-coordinate 447, and a row L511 of pixels starting at a y-coordinate 511 are taken for instance. Projection data items of lines T0 to T511 shown in FIG. 7 which result from projection of the rows L0 to L511 of pixels onto the surface of the multi-array X-ray detector 24 in the direction of X-ray transmission are sampled as projection data items Dr of the rows L0 to L511 of pixels.

The direction of X-ray transmission is determined with the geometric positions of the focal spot in the X-ray tube 21, the pixels, and the multi-array X-ray detector 24. A z-coordinate z(view) is appended to X-ray detector data D0(view,j,i) as a value indicating a position Ztable(view) in the z direction in which the table rectilinearly moves. Therefore, even if the projection data D0(view,j,i) is produced during acceleration or deceleration, the direction of X-ray transmission can be accurately detected.

When a line of projection data partly comes out of the multi-array X-ray detector 24 in the direction of channels in the same manner as, for example, the line T0 resulting from the projection of the row L0 of pixels onto the surface of the multi-array X-ray detector 24 in the direction of X-ray transmission does, the projection data Dr is set to 0s. Moreover, when part of a line comes out of the multi-array X-ray detector in the z direction, the projection data Dr is interpolated.

Consequently, as shown in FIG. 8, projection data items Dr(view,x,y) serving as the pixels contained in the scan field P are sampled.

Referring back to FIG. 5, at step S62, the projection data items Dr(view,x,y) are multiplied by cone beam reconstruction weighting coefficients in order to produce projection data items D2(view,x,y) shown in FIG. 9.

Herein, the cone beam reconstruction weighting coefficients w(i,j) will be described below. For reconstruction of a fan-shaped beam image, generally, assuming that an angle at which a straight line linking the focal spot in the X-ray tube 21 and a pixel g(x,y) in the scan field P (xy plane) at a view angle view=$\beta a$ meets the center axis Bc of the X-ray beam is $\gamma$ and the opposite view angle is view=$\beta b$, the opposite view angle is expressed as follows:

$$\beta b = \beta a + 180° - 2\gamma$$

Assuming that angles at which the X-ray beam passing through the pixel g(x,y) in the scan field P and the opposite X-ray beam meet the scan field P are $\alpha a$ and $\alpha b$ respectively, the products of back projection data items by cone-beam reconstruction weighting coefficients $\omega a$ and $\omega b$ that depend on the angles are added up in order to produce back projection pixel data D2(0,x,y).

$$D2(0,x,y) = \omega a \cdot D2(0,x,y)\_a + \omega b \cdot D2(0,x,y)\_b \quad \text{[Formula 7]}$$

The sum of the cone-beam reconstruction weighting coefficients, $\omega a + \omega b$, is a unity (1).

Since the products of the back projection data items by the cone-beam reconstruction weighting coefficients $\omega a$ and $\omega b$ are added up, cone-angle artifacts can be minimized.

For example, the cone-beam reconstruction weighting coefficients $\omega a$ and $\omega b$ may be calculated as described below.

Assuming that a half of the angle of a fan beam is $\gamma$max, the following relationships are established:

$$ga = f(\gamma max, \alpha a, \beta a)$$

$$gb = f(\gamma max, \alpha b, \beta b)$$

$$xa = 2 \cdot ga^q / (ga^q + gb^q)$$

$$xb = 2 \cdot gb^q / (ga^q + gb^q)$$

$$wa = xa^2 \cdot (3 - 2xa)$$

$$wb = xb^2 \cdot (3 - 2xb)$$

$$(\text{for example, } q = 1) \quad \text{[Formula 8]}$$

For example, assuming that max[ ] denotes a function providing a larger value, ga and gb are expressed as follows:

$$ga = max[0, \{(\pi/2 + \gamma max) - |\beta a|\}] \cdot |\tan(\alpha a)|$$

$$gb = max[0, \{(\pi/2 + \gamma max) - |\beta b|\}] \cdot |\tan(\alpha b)| \quad \text{[Formula 9]}$$

For fan beam image reconstruction, the pixels in the scan field P are multiplied by distance coefficients. Assuming that a distance from the focal spot in the X-ray tube 21 to a detector element that belongs to a detector array j and a channel i included in the multi-array X-ray detector 24 and that produces projection data Dr is r0, and a distance from the focal spot in the X-ray tube 21 to a pixel in the scan field P associated with the projection data Dr is r1, the distance coefficient is expressed as $(r1/r0)^2$.

For parallel-ray beam image reconstruction, the pixels in the scan field P are merely multiplied by the cone beam reconstruction weighting coefficients w(i,j).

At step S63, projection data items D2(view,x,y) are, as shown in FIG. 10, added to back projection data items D3(x, y) pixel by pixel.

At step S64, steps S61 to S63 are repeatedly executed for all views required for reconstruction of tomographic images (that is, views covering 360° or views covering 180°+the angle of a fan-shaped beam). This results in back projection data items D3(x,y) shown in FIG. 10.

Figure 11A:
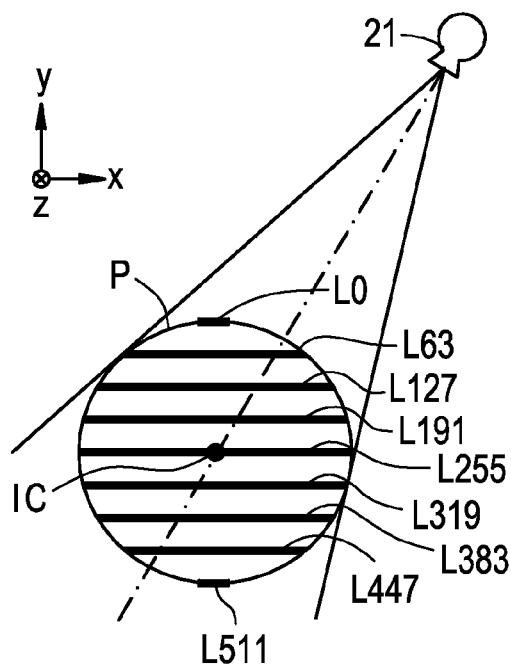
FIGS. 11a and 11b are conceptual diagrams showing projection of lines in a circular scan field in the direction of X-ray transmission.
Figure 11B:
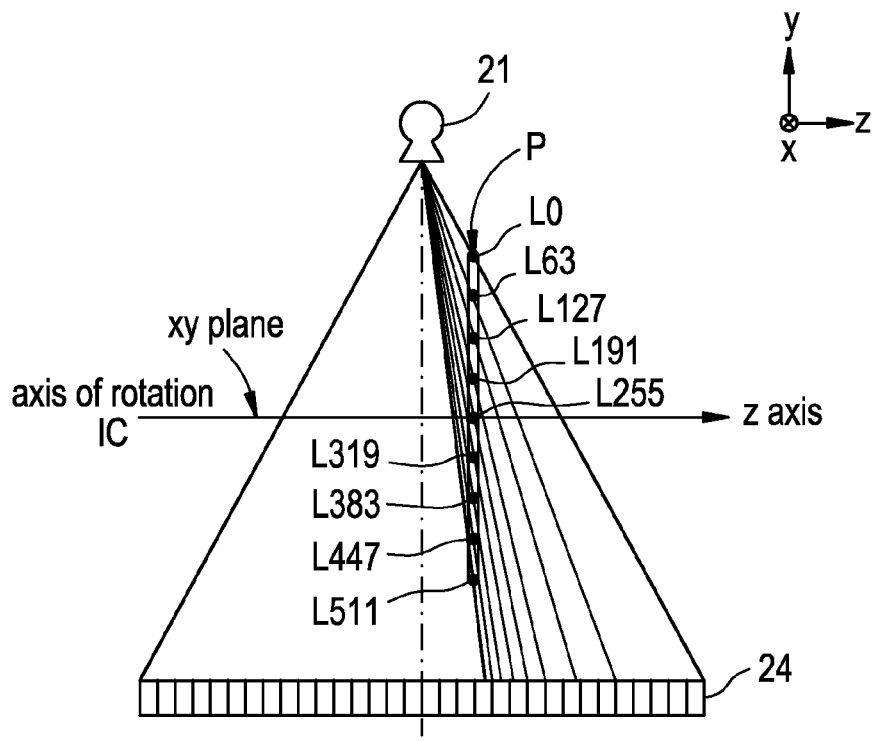

As shown in FIG. 11(a) and FIG. 11(b), the scan field P may be circular.

FIG. 12, FIG. 13, FIG. 17, FIG. 18, FIG. 19, FIG. 20, FIG. 23, FIG. 24, and FIG. 25 are concerned with compensation of deviations in the x and y directions of step S11 mentioned in FIG. 3.

Figure 12:
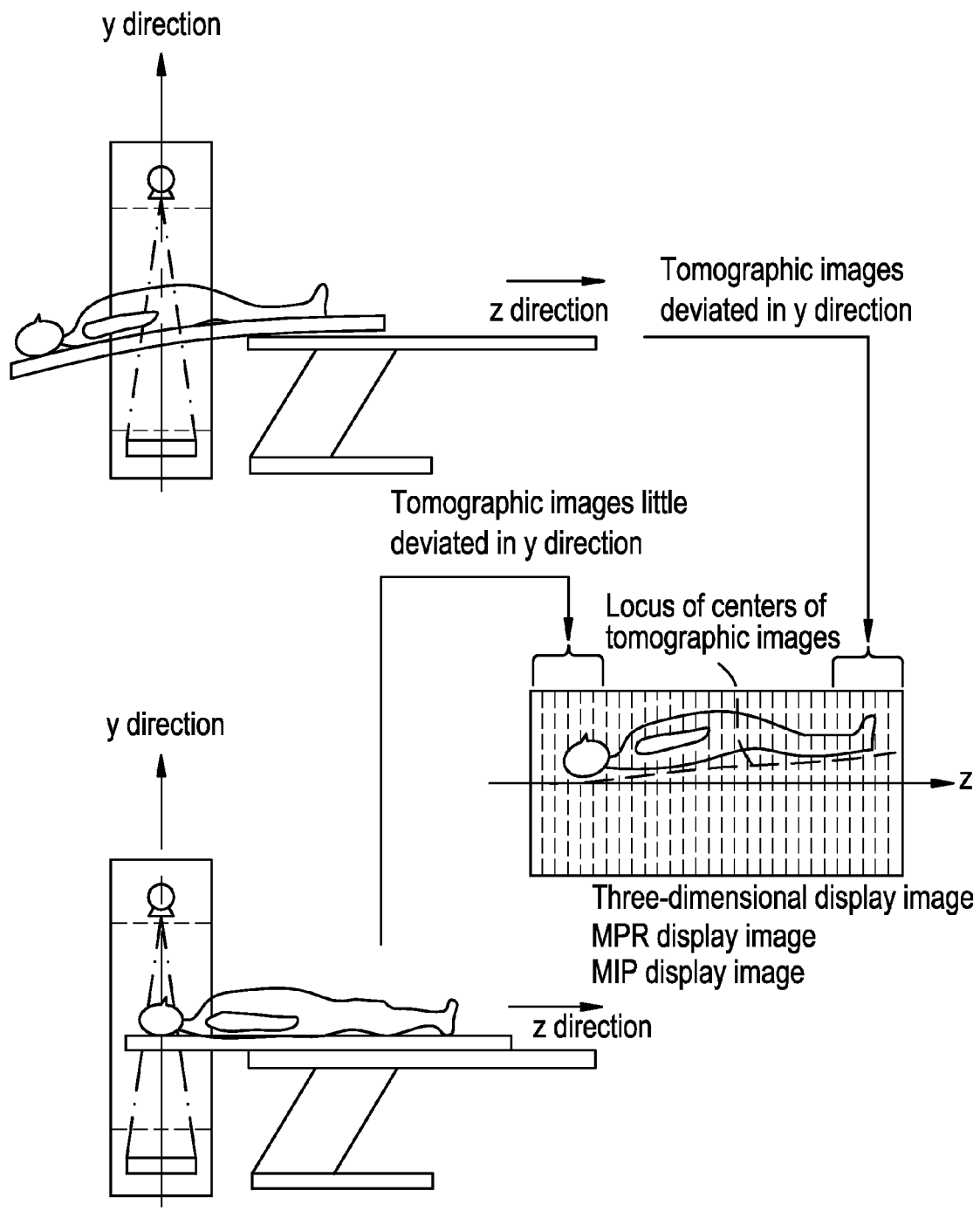
FIG. 12 shows deviations of the centers of tomographic images, which are produced by performing a helical scan, observed in a conventional three-dimensional display image, MPR display image, or MIP display image.

In the X-ray CT system, when the helical scanning is adopted, the centers of tomographic images are, as shown in FIG. 12, continuously deviated from one another along with the movement of the table in the z direction. When the conventional (axial) scanning or cine scanning is adopted, the centers of tomographic images, which are defined in the z direction and produced by performing a scan are deviated from one another on the xy plane along with the movement of the table in the z direction. This is attributable to the warp of the cradle or subject's body motions.

FIG. 17 shows magnitudes of deviations in the y direction of tomographic images defined in the z direction. In general, the deviations in the x and y direction of each of tomographic images produced by the X-ray CT system according to the conventional (axial) scanning, cine scanning, or helical scanning depend on a position in the z direction, and shall be denoted by Dx(Gi) and Dy(Gi) respectively.

The deviations Dx(Gi) and Dy(Gi) are measured as described below.

Figure 20:
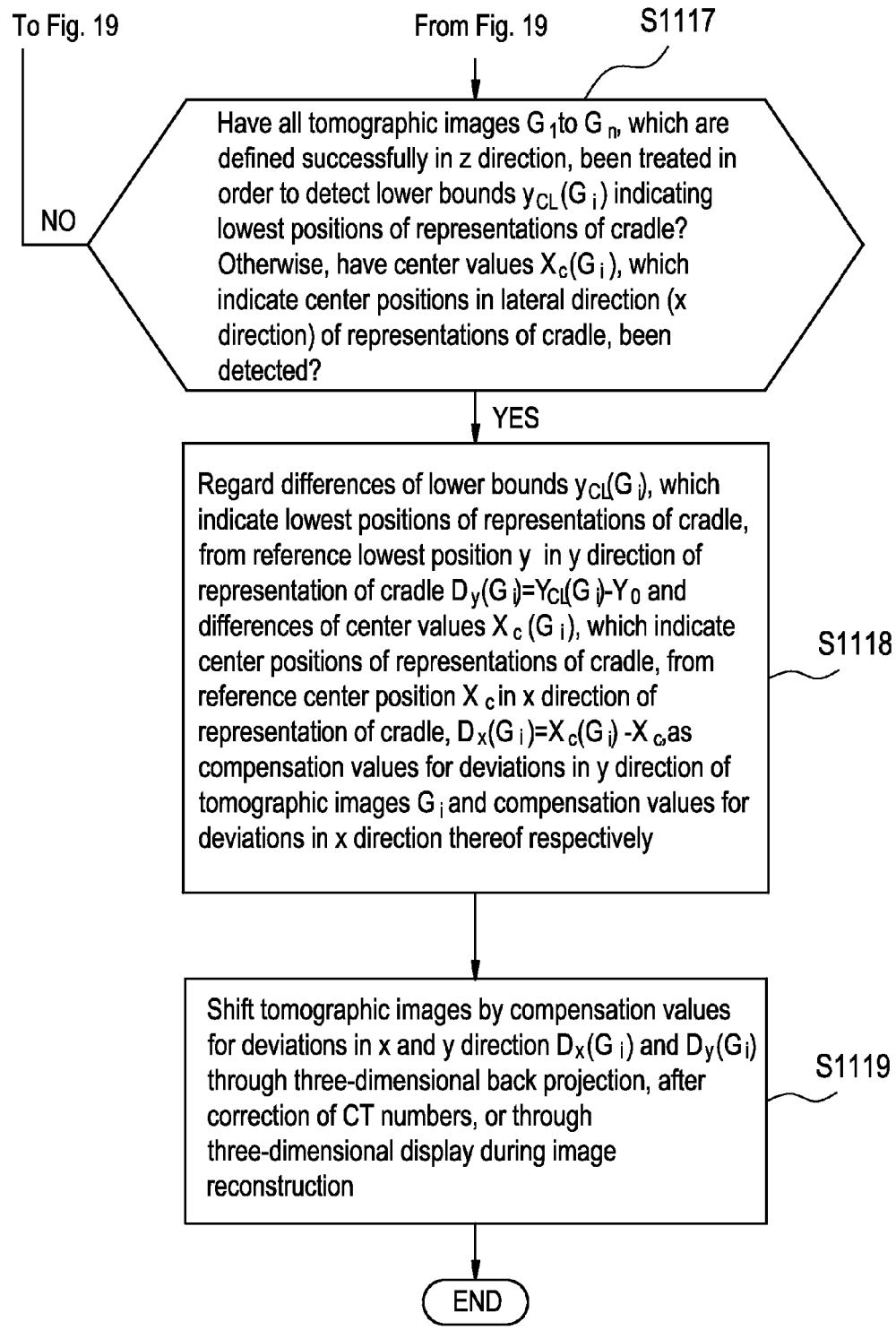
FIG. 20 describes the compensation of the deviations in the x and y directions according to a method of extracting characteristic parameters through characteristic parameter measurement.
Figure 23:
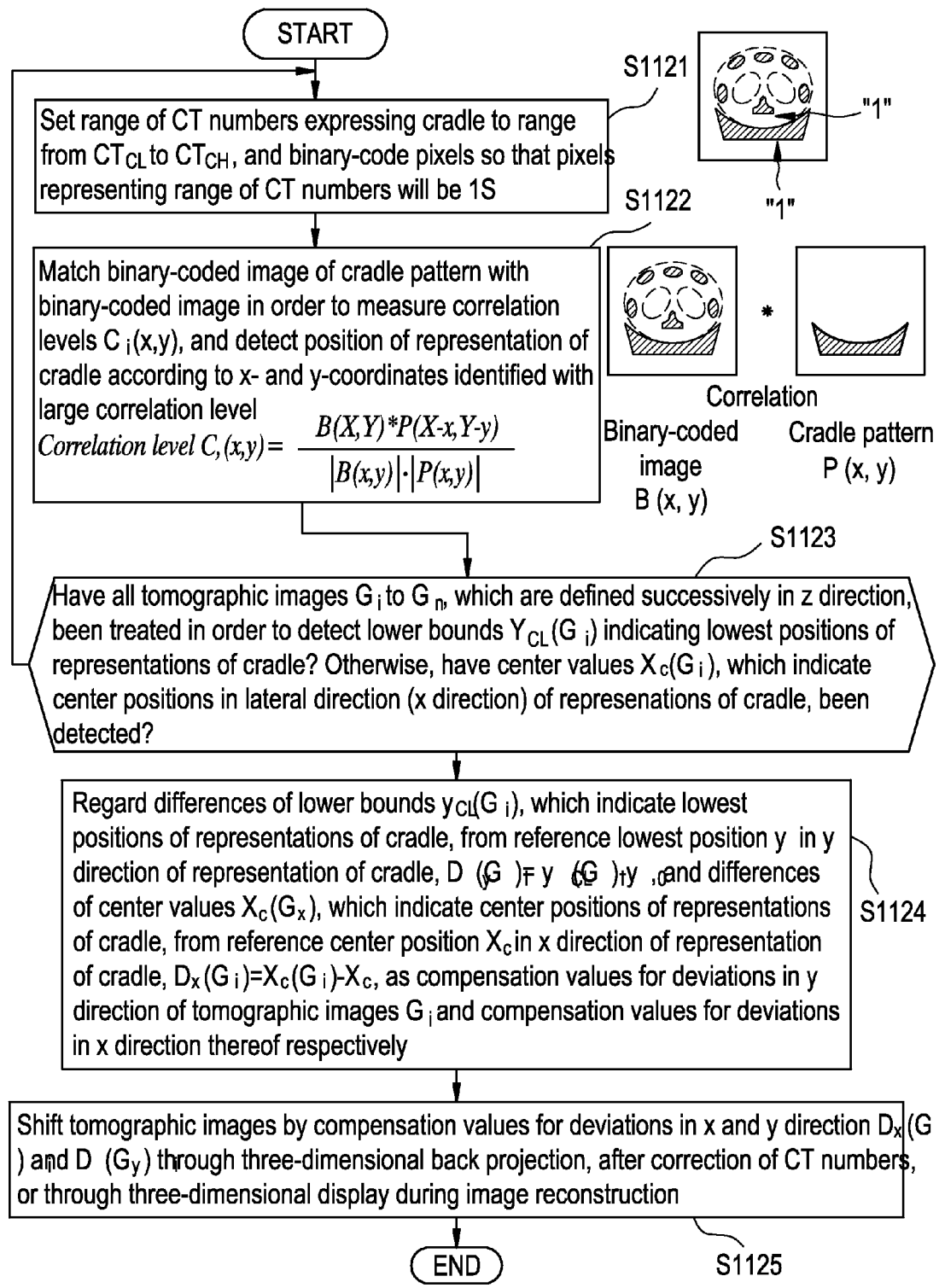
FIG. 23 shows compensation of deviations in the x and y direction according to a pattern matching method.

FIG. 18, FIG. 19, and FIG. 20 are concerned with a characteristic point extraction method, FIG. 23 is concerned with a pattern matching method, and FIG. 24 is concerned with a projection-data pattern matching method.

FIG. 18 describes a procedure to be followed according to the characteristic parameter method based on marginal distribution measurement.

If a partially enlarged tomographic image does not show the cradle, a scan field of view from which raw data items are acquired in order to produce projection data items is used to reconstruct an image that will show the cradle.

At step S1101, the range of CT numbers expressing the cradle is set to a range from a CT number $CT_{CL}$ to a Ct number $CT_{CH}$, and the pixels contained in a scan field are binary-coded so that pixels representing the range of CT numbers will be 1s. The binary coding brings the pixels expressing the cradle and part of a subject to 1s. Consequently, the shape and position of at least a representation of the cradle are extracted.

At step S1102, a profile (marginal distribution) is produced using values that are represented by pixels contained in a binary-coded image and that are derived from data items acquired in the x direction, and the lower bound $y_{CL}$ indicating the lowest position of a representation of the cradle is measured from data items acquired in the y direction. The number of pixels representing 1s in the binary-coded image produced at step S1102 is counted in the x direction, whereby the profile (marginal distribution) of the values measured in the x direction is produced. As shown in FIG. 16, the lowest point in the marginal distribution in the x direction corresponds to a coordinate expressing the bottom of the cradle, and the coordinate is regarded as the lower bound $y_{CL}$ that is a z-coordinate indicating the lowest position of the representation of the cradle.

At step S1103, all the tomographic images $G_1$ to $G_n$ defined in the z direction are checked to see if they are treated in order to detect the lower bounds $y_{CL}(Gi)$. If the lower bounds have not been detected, step S1101 is executed. If the lower bounds have been detected, step S1104 is executed. Consequently, the z-coordinates expressing the cradle in the tomographic images are detected.

At step S1104, the differences of the lower bounds $y_{CL}(G_i)$ indicating the lowest positions of the representations of the cradle from the reference position $y_0$ of the representation of the cradle in the y direction, $D_y(G_i)=y_{CL}(G_i)-y_0$, are regarded as compensation values for the deviations in the y direction of the tomographic images $G_i$. The deviations of the positions of the representations of the cradle in the tomographic images from the reference position $y_0$ of the representation of the cradle are calculated, and the compensation values for the deviations in the y direction are calculated.

At step S1105, the tomographic images are shifted by the compensation values $D(G_i)$ for the deviations in the y direction through three-dimensional back projection, after correction of CT numbers, or through three-dimensional display during image reconstruction. Consequently, the deviations in the x and y directions are compensated. When images are shifted during reconstruction for display, the centers of scan fields are shifted by the compensation values for the deviations. Thus, reconstructed tomographic images are shifted.

Instead of step S1102, the position of a representation of the cradle may be detected directly from a marginal distribution of projection data items.

Figure 30:
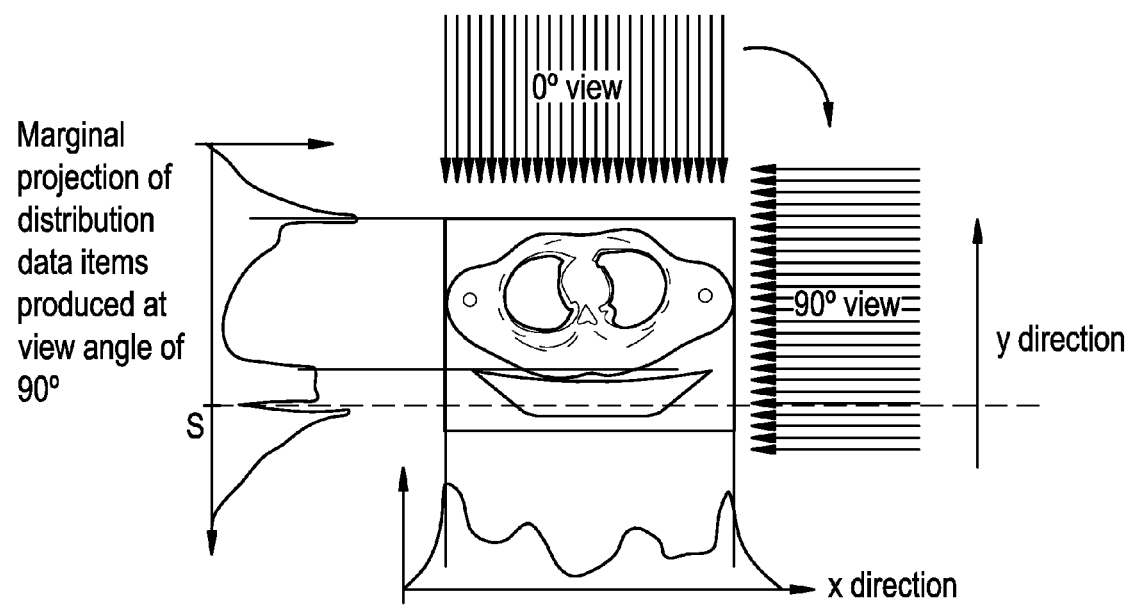
FIG. 30 illustratively shows a method for measuring marginal distributions using projection data items.

FIG. 30 shows marginal distributions of projection data items. The marginal distribution (profile) of projection data items produced at a view angle of 0° and the marginal distribution (profile) of projection data items produced at a view angle of 90° may be produced by re-projecting tomographic images. Otherwise, projection data items produced using a fan-shaped beam may be converted into projection data items to be produced using a parallel-ray beam, and the resultant data items may be defined equidistantly in the x or y direction. Even in this case, similarly to the case shown in FIG. 18, magnitudes of deviations of the positions of representations of the cradle occurring in the y direction can be measured.

A procedure to be followed according to a characteristic parameter extraction method based on characteristic parameter measurement mentioned in FIG. 19 and FIG. 20 will be described below.

If a partially enlarged tomographic image does not show the cradle, a scan field of view from which raw data items are acquired to produce projection data items is used to reconstruct a tomographic image that will show the cradle.

At step S1111, the range of CT numbers expressing the cradle is set to a range from a CT number $CT_{CL}$ to a CT number $CT_{CH}$. Pixels contained in a scan field are binary-coded so that the pixels representing the range of CT numbers will be 1s.

The binary coding brings the pixels expressing the cradle and part of a subject to 1s. Consequently, the shape and position of at least a representation of the cradle are extracted.

At step S1112, the binary-coded image is expanded by m1 times using a logical filter for expansion.

FIG. 21 shows an example of the logical filter for expansion.

At step S1113, the binary-coded image that has been expanded is contracted m2 times using a logical filter for contraction.

FIG. 22 shows an example of the logical filter for contraction.

At step S1114, continuous-bit domains are numbered through labeling.

The labeling may involve four or eight neighborhoods.

At step S1115, characteristic parameters of the respective domains are measured.

The characteristic parameter to be measured is thought to include an area, the lengthwise and sideways lengths of a circumscribed rectangle), a perimetric length, a roundness, a mean density (mean CT number), and a standard deviation of a density (CT number).

At step S1116, the characteristic parameters of the respective domains are logically checked in order to extract a domain expressing the cradle.

The permissible range of characteristic parameter values that can be recognized to express the cradle should be determined in advance. In this case, the permissible range of values of a characteristic parameter that relates to any of radiographic conditions should be determined in relation to each set of radiographic conditions.

At step S1117, all tomographic images $G_1$ to $G_n$ defined successively in the z direction are checked to see if they are treated in order to measure the lower bounds $y_{CL}(G_i)$ indicating the lowest positions of the representations of the cradle or the center values $X_c(G_i)$ indicating the center positions in the lateral direction (x direction) of the representations of the cradle. If all tomographic images $G_1$ to $G_n$ have not been treated, step S1111 is executed. If all tomographic images $G_1$ to $G_n$ have been treated, step S1118 is executed. Consequently, a z-coordinate indicating the position of the representation of the cradle in each of the tomographic images is detected.

At step S1118, the differences of the lower bounds $y_{CL}(G_i)$ indicating the lowest positions of the representations of the cradle from the reference lower position $y_0$ in the y direction of the representation of the cradle, $D_y(G_i)=y_{CL}(G_i)-y_0$, and the differences of the center values $X_c(G_i)$ indicating the center positions of the representations of the cradle from the reference center value $X_c$ indicating the center position in the x direction of the representation of the cradle, $D_x(G_i)=X_c(G_i)-X_c$, are regarded as the compensation values for the deviations in the y direction of the respective tomographic images Gi and the compensation values for the deviations in the x direction thereof respectively. Thus, the deviations of the positions of the representations of the cradle in the respective tomographic images from the reference position $y_0$ of the representation of the cradle are detected, and the compensation values for the deviations in the y direction are calculated.

At step S1119, the tomographic images are shifted by the compensation values $D_x(G_i)$ and $D_y(G_i)$ for the deviations in the x and y directions through three-dimensional back projection, after correction of CT numbers, or through three-dimensional display during image reconstruction. Consequently, the deviations in the x and y directions are compensated. When an image is shifted during image reconstruction, the center of a scan field is shifted by the compensation values for the deviations and the resultant scan field is used to reconstruct an image. Thus, a reconstructed tomographic image is shifted.

A procedure to be followed according to the pattern matching method mentioned in FIG. 23 will be described below.

Incidentally, if a partially enlarged tomographic image does not show the cradle, a scan field from which raw data items are acquired in order to produce projection data items is entirely used to reconstruct an image that will show the cradle.

At step S1121, the range of CT numbers expressing the cradle is set to a range from a CT number $CT_{CL}$ to a CT number $CT_{CH}$. Pixels are binary-coded so that the pixels representing the range of CT numbers will be 1s. The binary coding brings the pixels expressing the cradle and part of a subject to 1s. Consequently, the shape and position of at least a representation of the cradle are extracted.

At step S1122, a binary-coded image of a standard cradle pattern that is registered in advance is matched with a binary-coded image in order to measure correlation levels Ci(x,y). A position indicated by an x-coordinate and a y-coordinate identified with a large correlation level refers to the position of the representation of the cradle.

$$\text{Correlation level } C_i(x,y) = \frac{B(X,Y)*P(X-x,Y-y)}{|B(x,y)|\cdot|P(x,y)|} \quad \text{[Formula 10]}$$

The correlation level $C_i(x,y)$ is calculated by scanning the standard cradle pattern, which is registered in advance, in the x direction and then in the y direction, and by scanning all points in an image indicated by an x-coordinate and a y-coordinate. When a domain expressing a similar shape fits the cradle pattern, the correlation level assumes a large value. If the fact that a tomographic image shows the cradle is known in advance, the point identified with the correlation level $C_i(x,y)$ assuming the largest value is recognized as the position of the representation of the cradle.

For calculation of the correlation level $C_i(x,y)$, the standard cradle pattern registered in advance and a tomographic image to be checked to see if it shows the cradle may be binary-coded images or gray-level images represented by gray levels (CT numbers). In general, the employment of gray-level images is known to ensure higher precision in position detection.

At step S1123, all tomographic images $G_1$ to $G_n$ defined successively in the z direction are checked to see if they are treated to measure the lower bounds $y_{CL}(G_i)$ indicating the lowest positions of the representations of the cradle or to measure the center values $X_c(G_i)$ indicating the center positions in the lateral direction (x direction) of the representations of the cradle. If all tomographic images $G_1$ to $G_n$ have not been treated, step S1121 is executed. If all tomographic images $G_1$ to $G_n$ have been treated, step S1124 is executed. Consequently, a z-coordinate indicating the position of the representation of the cradle in each of the tomographic images is detected.

At step S1124, the differences of the lower bounds $y_{CL}(G_i)$ from the reference lowest position $y_0$ in the y direction of the representation of the cradle, $D_y(G_i)=y_{CL}(G_i)-y_0$, and the differences of the center values $X_c(G_i)$ indicating the center positions of the representations of the cradle from the reference center position $X_c$ in the x direction of the representation of the cradle, $D_x(G_i)=X_c(G_i)-X_c$, are regarded as the compensation values for the deviations in the y direction of the respective tomographic images $G_i$ and the compensation values for the deviations in the x direction thereof respectively. Consequently, the deviations of the positions of the representations of the cradle in the respective tomographic images from the reference position $y_0$ of the representation of the cradle are measured, and the compensation values for the deviations in the y direction are measured.

At step S1125, the tomographic images are shifted by the compensation values $D_x(G_i)$ and $D_y(G_i)$ for the deviations in the x and y directions through three-dimensional back projection, after correction of CT numbers, or through three-dimensional display during image reconstruction. Consequently, the deviations in the x and y directions are compensated. When an image is shifted during image reconstruction, the center of a scan field is shifted by the compensation values for the deviations and the resultant scan field is then used to reconstruct an image. Thus, a reconstructed tomographic image is shifted.

A procedure to be followed according to the projection data pattern matching method mentioned in FIG. 24 will be described below.

Incidentally, if a partially enlarged tomographic image does not show the cradle, a scan field from which raw data items are acquired in order to produce projection data items is entirely used to reconstruct an image that will show the cradle.

At step S1131, projection data items $ProjC(\theta,S)$ are produced in advance by irradiating X-rays to the cradle in directions of projection $\theta$. Otherwise, re-projection is performed in order to produce the projection data items $ProjC(\theta,S)$.

In order to correlate projection data items with projection data items that are produced by irradiating X-rays to the cradle in a direction $\theta$ and registered in advance, data items contained in tomographic images and acquired in the direction $\theta$ are re-projected in order to produce the projection data items. At step S1132, the projection data items $ProjC(\theta,S)$ produced at step S1131 by re-projecting data items acquired from the cradle in each of the directions of projection are correlated with the projection data items $ProjC(\theta,S)$ produced by irradiating X-rays to a subject in each of the same directions $\theta$ of projection. Consistent coordinates $S(\theta)$ are then measured. These steps are executed for all directions of projection $\theta$ in order to measure the consistent coordinates $S(\theta)$. The values of correlation $C(S,\theta)$ among the projection data items produced by projecting X-rays to the cradle in the directions θ and registered in advance, the projection data items that are produced by re-projecting data items contained tomographic images and acquired in the directions θ, and the projection data items produced by re-projecting tomographic images are checked in order to measure the coordinate S(θ) identified with the largest correlation values C(S,θ).

At step S1133, the locus of the coordinates S(θ) measured at step S1132 is fitted to a sine curve A=sin(θ+a)in order to detect optimal values A and a. The cradle is located at a distance of A from the center of rotation. The position of the cradle is detected in a direction a determined with an angle of projection.

At step S1134, all tomographic images $G_1$ to $G_n$ defined successively in the z direction are checked to see if they are treated in order to measure the lower bounds $y_{CL}(G_i)$ indicating the lowest positions of representations of the cradle or the center values $X_c(G_i)$ indicating the center positions in the lateral direction (x direction) of the representations of the cradle. If all tomographic images $G_1$ to $G_n$ have not been treated, step S1131 is executed. If all tomographic images $G_1$ to $G_n$ have been treated, step S1135 is executed. Consequently, the z-coordinates indicating the positions of the representations of the cradle in the respective tomographic images can be detected.

At step S1135, the differences of the lower bounds $y_{CL}(G_i)$ indicating the lowest positions of the representations of the cradle from the reference lowest position $y_0$ in the y direction of the representation of the cradle, $D_y(G_i)=y_{CL}(G_i)-y_0$, and the differences of the center values $X_c(G_i)$ indicating the center positions of the representations of the cradle from the reference center position $X_c$ in the x direction of the representation of the cradle, $D_x(G_i)=X_c(G_i)-X_c$, are regarded as the compensation values for the deviations in the y and x directions of the respective tomographic images $G_i$. Consequently, the deviations of the positions of the representations of the cradle in the respective tomographic images from the reference position $y_0$ of the representation of the cradle are recognized, and the compensation values for the deviations in the y direction are measured.

At step S1136, the tomographic images are shifted by the compensation values $D_x(G_i)$ and $D_y(G_i)$ for the deviations in the x and y directions through three-dimensional back projection, after correction of CT numbers, or through three-dimensional display during image reconstruction. Consequently, the deviations in the x and y directions are compensated. When an image is shifted through image reconstruction, the center of a scan field is shifted by the compensation values for the deviations and the resultant scan field is used to reconstruct an image. Thus, the reconstructed tomographic image is shifted.

Figure 28:
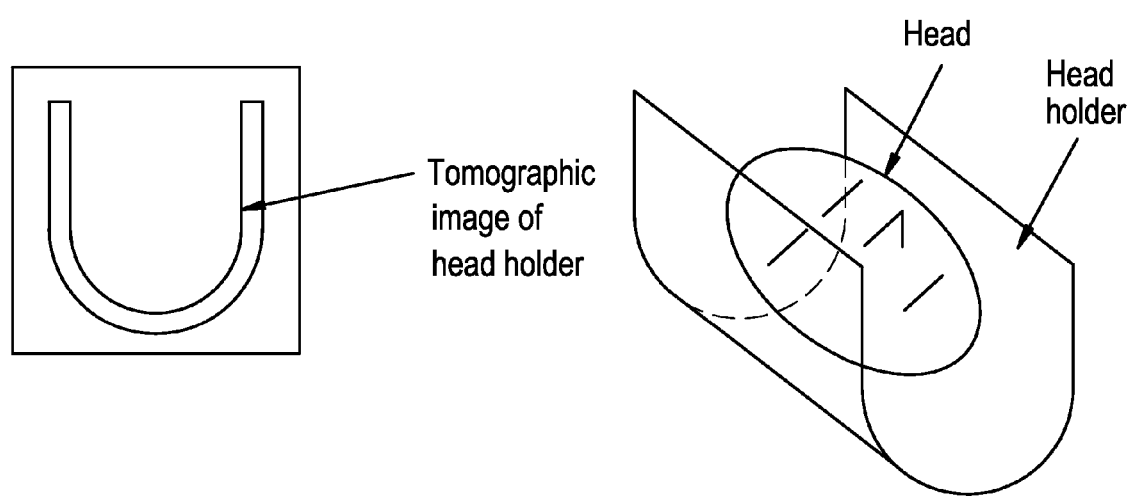
FIG. 28 shows a head holder for holding the head.

In the above description, the cradle is used to present a reference position for tomographic images. Especially when the head is scanned, a head holder shown in FIG. 28 may be used to present the reference position. A characteristic parameter may be measured in order to detect the position of a representation of the head holder, or a correlation function may be used to detect the position.

In consideration of the continuity of a subject, subject's motions defined on an xy plane may be detected using pixels that represent high CT numbers expressing the surface of the subject or the bone thereof, and deviations in the x and y directions of tomographic images may be compensated based on the detected motions.

Figure 29:
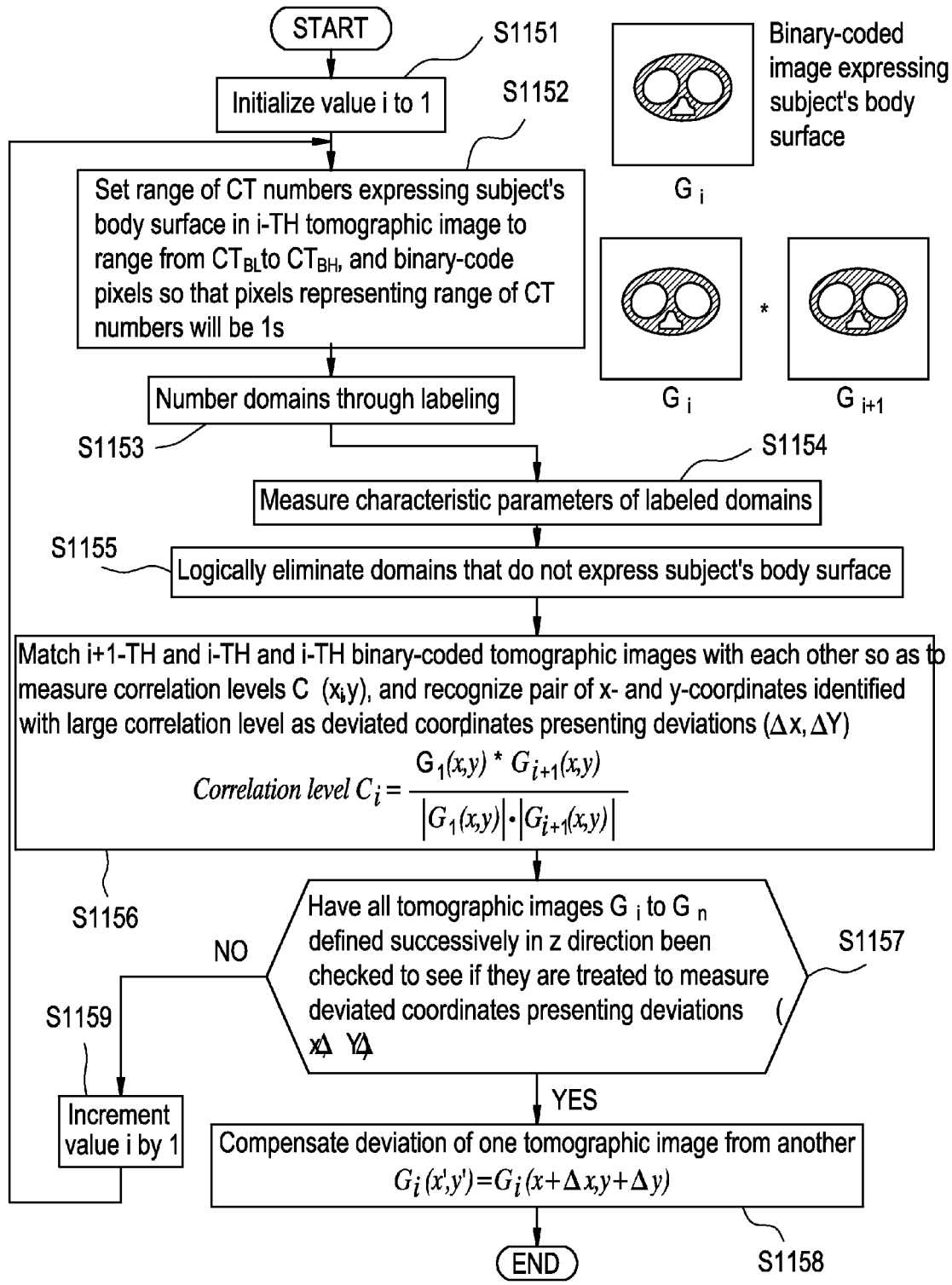
FIG. 29 describes correction of deviated x- and y-coordinates using a subject's body surface as a reference.

FIG. 29 is a flowchart describing correction of deviated x-coordinates and y-coordinates using the surface of a subject's body as a reference.

At step S1151, a value i is initialized to 1.

At step S1152, the range of CT numbers expressing the surface of a subject's body in the i-th tomographic image is set to a range from a CT number $CT_{BL}$ to a CT number $CT_{BH}$. Pixels constituting the i-th tomographic image are binary-coded so that the pixels representing the range of CT numbers will be 1s.

At this time, a range of CT numbers permitting elimination of representations of the cradle and other objects abutted on the subject's body surface is determined.

At step S1153, numbering (labeling) is performed.

If labeling fails due to noises in the image, the aforesaid expansion logical filter and contraction filter are used to refine a counter line. Labeling is then performed again.

At step S1154, characteristic parameters of labeled domains are measured.

At step S1155, domains that do not express the subject's body surface are logically eliminated.

For effective extraction of a domain expressing the subject's body surface, a logic or a threshold relative to which domains are checked should be varied depending on a region such as the subject's head or abdomen.

At step S1156, the i+1-th and i-th binary-coded tomographic images are matched with each other in order to measure correlation levels $C_i(x,y)$. A pair of coordinates (x,y) identified with a large correlation level are recognized as deviated coordinates presenting deviations (Δx,Δy).

$$\text{Correlation level } C_i = \frac{G_1(X, Y) * G_{i+1}(x, y)}{|G_1(x, y)| \cdot |G_{i+1}(x, y)|} \quad [\text{Formula 11}]$$

In this case, instead of calculating correlation levels using binary-coded images, gray-scale images may be used to calculate correlation levels. The employment of gray-scale images would improve precision.

At step S1157, all the tomographic images $G_1$ to $G_n$ defined in the z direction are checked to see if they are treated in order to measure deviated coordinates p resenting deviations (Δx, Δy). If all the tomographic images $G_1$ to $G_n$ have been treated, control is passed to step S1158. If all the tomographic images $G_1$ to $G_n$, have not been treated, control is passed to step S1159.

At step S1158, a deviation of one tomographic image from another is compensated.

$$G_i(x',y')=G_i(x+\Delta x,y+\Delta y) \quad [\text{Formula 12}]$$

At step S1159, the tomographic image number is incremented. Control is then returned to step S1152, and the next tomographic image is treated.

FIRST EXAMPLE

The first example will be described in relation to conventional (axial) scanning or cine scanning.

specifically, at step S1, as shown in FIG. 14, the cradle 12 of the radiographic table 10 is moved in units of a length equal to or smaller than the width D on the z axis of an X-ray beam passing through the center of rotation. A conventional (axial) or cine scan is performed in order to acquire data items from subject's slices juxtaposed in the z direction, whereby X-ray detector data items are acquired. Herein, X-ray detector data items D0(view,j,i) are each identified with a view angle view, a detector array number j, and a channel number i, and each appended a position in the z direction in which the table is moved rectilinearly, Ztable(view).

When a conventional (axial) scan or a cine scan is continuously performed in the z direction, the scan may be, as shown in FIG. 15, continuously performed in the z direction without an interval between successive scans. The conventional (axial) scan or cine scan may be, as shown in FIG. 16, continuously performed in the z direction so that successive scans will partly coincide with one another. In the case of FIG. 16, since image quality is degraded because of a large cone angle, that is, a large angle of an X-ray beam defined by planes containing outer ones of the arrays of X-ray detector elements, which are juxtaposed in the z direction and included in a multi-array X-ray detector or a two-dimensional X-ray area detector, a scan may be performed continuously in the z direction so that successive scans will partly coincide with one another. Image quality may be improved by adding up tomographic images.

At step S2, the aforesaid pre-processing is performed.

At step S3, beam hardening artifacts are compensated.

At step S4, a z-filter is used to perform convolution.

At step S5, a reconstruction function is used to perform convolution.

At step S6, three-dimensional back projection is performed.

Compensation of deviations in the y direction or in the x and y direction of step S11 and compensation of deviations in the z direction of step S21 may be performed during image reconstruction of step S6 or during image display of step S7 or step S8.

When the projection data pattern matching method is adopted as described at steps S1131 to S1136 in FIG. 24, the positions of the representations of the cradle in respective tomographic images to be used as references are detected according to the projection data pattern matching method at any of steps S2, S3, S4, and S5. During three-dimensional back projection of step S6, the center of a scan field is shifted by compensation values for deviations. Thus, the deviations in the x and y directions are compensated.

A deviation in the y direction may be compensated by extracting characteristic parameters through measurement of marginal distributions as mentioned at step S1101 to S1105 in FIG. 18.

Deviations in the x and y directions may be compensated by extracting characteristic parameters through measurement of the characteristic parameters as mentioned at steps S1111 to S1116 in FIG. 19.

Deviations in the x and y directions may be compensated according to the pattern matching method as mentioned at steps S1121 to S1125 in FIG. 19. According to the three methods of the characteristic parameter extraction method based on marginal distribution measurement, the characteristic parameters extraction method based on characteristic parameter measurement, and the pattern matching method, tomographic images reconstructed through three-dimensional back projection are used to measure deviations. Deviations in the y direction or deviations in the x and y directions may be compensated during post-processing of step S7, tomographic image display of step S8, or three-dimensional image display of step S9. Even when the projection data matching method is adopted as mentioned in FIG. 24, the deviations in the y direction or the deviations in the x and y directions are compensated during post-processing of step S7, tomographic image display of step S8, or three-dimensional image display of step S9.

Actions are performed as described in FIG. 26.

At step H1, a conventional (axial) scan, a cine scan, or a helical scan is continuously performed in order to reconstruct tomographic images.

At step H2, the heights of the cradle 12 attained in places where images are reconstructed and the positions of the places are calculated.

At step H3, the heights of the cradle 12 calculated at step H2 are used to calculate coordinate vectors representing deviations in the x and y directions or deviations in the y direction occurring at positions in the z direction.

At step H4, the coordinate vectors representing deviations in the x and y directions or deviations in the y direction are recorded in a file containing image data or a file other than the file of image data.

At step H5, the coordinate vectors representing deviations and being calculated at step H3 are used to compensate the deviations in the y direction or the deviations in the x and y directions during three-dimensional image display, MPR image display, or MIP image display.

In conventional (axial) scanning or cine scanning, coordinates indicating scanned positions in the z direction in which the table is moved are measured during each scan. Thus, the deviations in the z direction may be compensated.

SECOND EXAMPLE

In the second example, helical scanning is employed. The deviations in the y direction of all tomographic images are not compensated but the deviations therein of thinned tomographic images are compensated. The same advantages can be expected as the advantages provided with employment of conventional (axial) scanning or cine scanning.

Figure 27:
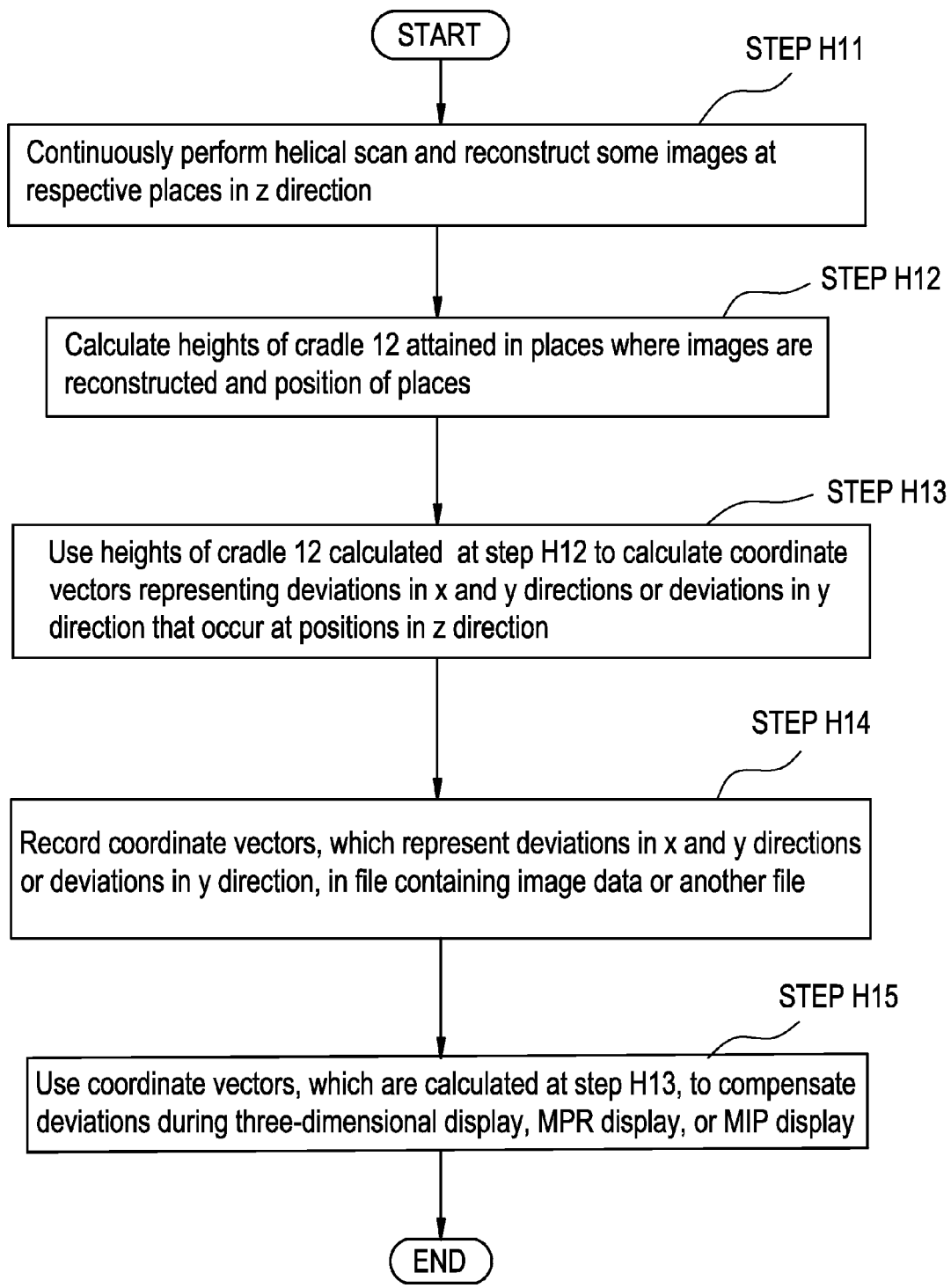
FIG. 27 describes an example of correcting deviated coordinates, which are derived from a continuous helical scan, during image display while thinning positions in the z direction at which deviations are compensated.

FIG. 27 is a flowchart describing the procedure.

At step H1, a helical scan is continuously performed. Some tomographic images are reconstructed in respective places in the z direction.

At step H2, the heights of the cradle 12 attained in the places where images are reconstructed and the positions of the places are calculated.

At step H3, the heights of the cradle 12 calculated at step H2 are used to calculate coordinate vectors representing the deviations in the y direction that occur at positions in the z direction.

At step H4, the coordinate vectors representing the deviations in the y direction are recorded as part of image data.

At step H5, the coordinate vectors representing the deviations calculated at step H3 are used to compensate the deviations during three-dimensional display, MPR display, or MIP display.

THIRD EXAMPLE

Figure 31:
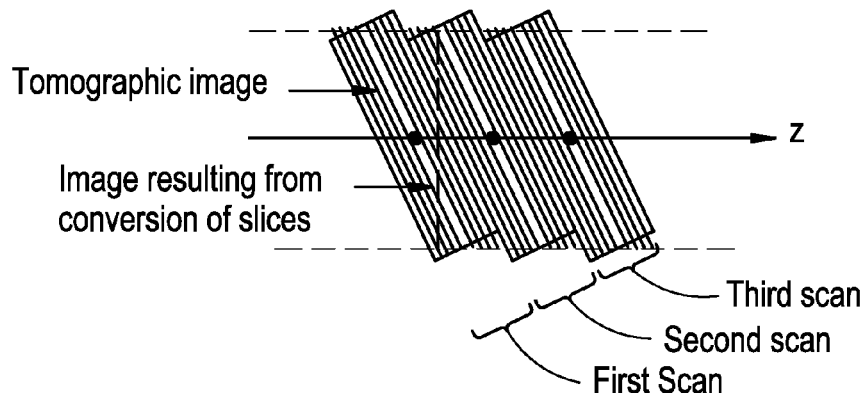
FIG. 31 shows conversion of slices imaged by continuously performing a conventional (axial) scan or a cine scan with a scanner gantry tilted.

In the third example, as shown in FIG. 31, a conventional (axial) scan or a cine scan is continuously performed at scanned positions with the scanner gantry 20 tilted. Since the deviations in the x and y directions, the deviations in the y direction, or the deviations in the x, y, and z directions are compensated, an image resulting from conversion of slices would enjoy better quality than it conventional does.

FOURTH EXAMPLE

Figure 32:
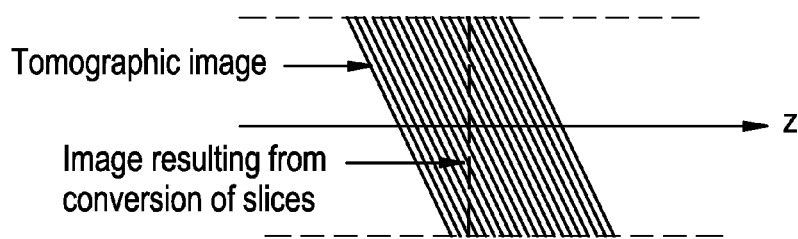
FIG. 32 shows conversion of slices imaged by continuously performing a helical scan with the scanner gantry tilted.

In the fourth example, as shown in FIG. 32, a helical scan is continuously performed with the scanner gantry 20 tilted. The produced tomographic images are treated in order to compensate the deviations in the x and y directions, the deviations in the y direction, or the deviations in the x, y, and z directions thereof. An image resulting from conversion of slices would enjoy better quality than it conventional does.

In the X-ray CT system 100, if an X-ray CT system or an X-ray CT imaging method in accordance with the present invention is implemented, the quality of a three-dimensional display image, an MPR display image, or an MIP display image produced by continuously performing a conventional (axial) scan, a cine scan, or a helical scan can be improved.

As for an image reconstruction method, a three-dimensional image reconstruction method based on the known Feldkamp technique may be adopted. Any other three-dimensional image reconstruction method or a two-dimensional image reconstruction method will do.

Furthermore, in the present embodiment, filtering coefficients to be convoluted to projection data items produced by detector elements juxtaposed in the direction of arrays (z direction) are varied depending on a detector array. Especially when the conventional (axial) scanning is adopted, a difference in image quality derived from a difference in a cone angle is adjusted so that each detector array can realize an even slice thickness and ensure even image quality in terms of artifacts and noises. The filtering coefficients may be presumably determined in various manners. In any way, the same advantages can be provided.

The present invention can be applied not only to X-ray CT systems for medical use but also to X-ray CT systems for industrial use or X-ray CT systems combined with any other system such as an X-ray CT PET system and an X-ray CT SPECT system.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT system comprising:
an X-ray data collection device for enabling an X-ray generator and an X-ray area detector, which is opposed to the X-ray generator in order to detect X-rays and structured with detector elements arranged in the form of a matrix, to rotate about a center of rotation located between them, and collect projection data items produced from X-rays transmitted by a subject lying on a subject support unit between the X-ray generator and the X-ray area detector;
an image reconstruction device for reconstructing a plurality of tomographic images corresponding to each position in a body axis direction of the subject by using the projection data items collected by the X-ray data collection device; and
an image display device for displaying the plurality of reconstructed tomographic images;
wherein at least one of the image reconstruction device and the image display device is configured to:
detect a reference point in each of the plurality of reconstructed tomographic images;
measure a deviation of each of the plurality of reconstructed tomographic images in a y direction that is a height direction of the subject support unit, or a deviation thereof in an x direction that is a width direction of the subject support unit and the y direction by identifying a position of a reference point in each of the plurality of reconstructed tomographic images and specifying a difference between each reference point position, wherein each reference point is located at an outer edge of the subject support unit;
compensate for the deviations so as to minimize a difference between each reference point position; and
produce at least one of a three-dimensional display image, a multiplanar reformation display image, and a maximum-intensity projection display image using the compensated plurality of reconstructed tomographic images.

2. The X-ray CT system according to claim 1, wherein the image display device detects a reference point in each of the plurality of reconstructed tomographic images using projection data corresponding to the reconstructed tomographic images.

3. The X-ray CT system according to claim 1, wherein the reconstruction device detects a reference point in each of the plurality of reconstructed tomographic images using CT values of the reconstructed tomographic images.

4. The X-ray CT system according to claim 1, wherein specifying a difference between each reference point position comprises using a characteristic parameter extraction method that is to extract a reference point based on a profile of the y-direction or the x-direction and the y-direction of the tomographic images.

5. The X-ray CT system according to claim 1, specifying a difference between each reference point position comprises using a characteristic parameter extraction method that is to extract a reference point by measuring a characteristic parameter based on a predetermined logical filter.

6. The X-ray CT system according to claim 1, wherein specifying a difference between each reference point position comprises using a pattern matching method that extracts a reference point by comparing the reference point with a predetermined standard pattern.

7. An X-ray CT system comprising:
an X-ray data collection device for enabling an X-ray generator and an X-ray area detector, which is opposed to the X-ray generator in order to detect X-rays and structured with detector elements arranged in the form of a matrix, to rotate about a center of rotation located between them, and collect projection data items produced from X-rays transmitted by a subject lying on a subject support unit between the X-ray generator and the X-ray area detector;
an image reconstruction device for reconstructing a plurality of tomographic images corresponding to each position in a body axis direction of the subject by using the projection data items collected by the X-ray data collection device; and
an image display device for displaying the plurality of reconstructed tomographic images;
wherein at least one of the image reconstruction device and the image display device is configured to:
detect a reference point in each of the plurality of reconstructed tomographic images;
measure a deviation of each of the plurality of reconstructed tomographic images in a y direction that is a height direction of the subject support unit, or a deviation thereof in an x direction that is a width direction of the subject support unit and the y direction by identifying a position of a reference point in each of the plurality of reconstructed tomographic images and specifying a difference between each reference point position, wherein each reference point is a part of the subject;
compensate for the deviations so as to minimize a difference between each reference point position; and
produce at least one of a three-dimensional display image, a multiplanar reformation display image, and a maximum-intensity projection display image using the compensated plurality of reconstructed tomographic images.

8. The X-ray CT system according to claim 7, wherein the image display device detects a reference point in each of the plurality of reconstructed tomographic images using projection data corresponding to the reconstructed tomographic images.

9. The X-ray CT system according to claim 7, wherein the reconstruction device detects a reference point in each of the plurality of reconstructed tomographic images using CT values of the reconstructed tomographic images.

10. The X-ray CT system according to claim 7, wherein specifying a difference between each reference point position comprises using a characteristic parameter extraction method that is to extract a reference point based on a profile of the y-direction or the x-direction and the y-direction of the tomographic images.

11. The X-ray CT system according to claim 7, specifying a difference between each reference point position comprises using a characteristic parameter extraction method that is to extract a reference point by measuring a characteristic parameter based on a predetermined logical filter.

12. The X-ray CT system according to claim 7, wherein specifying a difference between each reference point position comprises using a pattern matching method that extracts a reference point by comparing the reference point with a predetermined standard pattern.

13. The X-ray CT system according to claim 7, wherein the reference point is located at surface of the subject or a bone in the subject.

14. An X-ray CT system comprising:
an X-ray data collection device for enabling an X-ray generator and an X-ray area detector, which is opposed to the X-ray generator in order to detect X-rays and structured with detector elements arranged in the form of a matrix, to rotate about a center of rotation located between them, and collect projection data items produced from X-rays transmitted by a subject lying on a subject support unit between the X-ray generator and the X-ray area detector;
a head holder for supporting a head of the subject;
an image reconstruction device for reconstructing a plurality of tomographic images corresponding to each position in a body axis direction of the subject by using the projection data items collected by the X-ray data collection device; and
an image display device for displaying the plurality of reconstructed tomographic images;
wherein at least one of the image reconstruction device and the image display device is configured to:
detect a reference point in each of the plurality of reconstructed tomographic images;
measure a deviation of each of the plurality of reconstructed tomographic images in a y direction that is a height direction of the subject support unit, or a deviation thereof in an x direction that is a width direction of the subject support unit and the y direction by identifying a position of a reference point in each of the plurality of reconstructed tomographic images and specifying a difference between each reference point position, wherein each reference point is located at a holder for a head of the subject;
compensate for the deviations so as to minimize a difference between each reference point position; and
produce at least one of a three-dimensional display image, a multiplanar reformation display image, and a maximum-intensity projection display image using the compensated plurality of reconstructed tomographic images.

15. The X-ray CT system according to claim 14, wherein the image display device detects a reference point in each of the plurality of reconstructed tomographic images using projection data corresponding to the reconstructed tomographic images.

16. The X-ray CT system according to claim 14, wherein the reconstruction device detects a reference point in each of the plurality of reconstructed tomographic images using CT values of the reconstructed tomographic images.

17. The X-ray CT system according to claim 14, wherein specifying a difference between each reference point position comprises using a characteristic parameter extraction method that is to extract a reference point based on a profile of the y-direction or the x-direction and the y-direction of the tomographic images.

18. The X-ray CT system according to claim 14, specifying a difference between each reference point position comprises using a characteristic parameter extraction method that is to extract a reference point by measuring a characteristic parameter based on a predetermined logical filter.

19. The X-ray CT system according to claim 14, wherein specifying a difference between each reference point position comprises using a pattern matching method that extracts a reference point by comparing the reference point with a predetermined standard pattern.

* * * * *